United States Patent
Li et al.

(10) Patent No.: US 9,655,522 B2
(45) Date of Patent: May 23, 2017

(54) METHOD AND SYSTEM FOR "PUSH-BUTTON" COMPREHENSIVE CARDIAC MR EXAMINATION USING CONTINUOUS SELF-GATED 3D RADIAL IMAGING

(71) Applicant: Cedars-Sinai Medical Center, Los Angeles, CA (US)

(72) Inventors: Debiao Li, South Pasadena, CA (US); Behzad Sharif, Los Angeles, CA (US); Daniel S. Berman, Los Angeles, CA (US); Jianing Pang, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 27 days.

(21) Appl. No.: 14/878,937

(22) Filed: Oct. 8, 2015

(65) Prior Publication Data
US 2016/0104279 A1    Apr. 14, 2016

Related U.S. Application Data

(60) Provisional application No. 62/062,781, filed on Oct. 10, 2014.

(51) Int. Cl.

| | |
|---|---|
| *G06K 9/00* | (2006.01) |
| *A61B 5/00* | (2006.01) |
| *G06K 9/52* | (2006.01) |
| *A61B 5/055* | (2006.01) |
| *G01R 33/565* | (2006.01) |
| *G06T 7/33* | (2017.01) |
| *G01R 33/48* | (2006.01) |

(Continued)

(52) U.S. Cl.
CPC .......... *A61B 5/0044* (2013.01); *A61B 5/055* (2013.01); *G01R 33/56509* (2013.01); *G06K 9/52* (2013.01); *G06T 7/337* (2017.01); *G01R 33/4826* (2013.01); *G01R 33/4838* (2013.01); *G01R 33/5602* (2013.01); *G01R 33/5608* (2013.01); *G01R 33/5611* (2013.01); *G01R 33/5635* (2013.01); *G01R 33/56325* (2013.01); *G01R 33/56366* (2013.01); *G06T 2207/10016* (2013.01); *G06T 2207/10088* (2013.01); *G06T 2207/30048* (2013.01)

(58) Field of Classification Search
CPC ... G06T 7/00; G06T 11/00; G06T 7/20; A61B 5/00; A61B 5/055; G06K 9/52
USPC .......................................... 382/131
See application file for complete search history.

(56) References Cited

PUBLICATIONS

Pang, J. et al., ECG and navigator-free 4D whole-heart coronary MRA for simultaneous visualization of cardiac anatomy and function, Magn Reson Med., 2014, 72(5):1-22.*

(Continued)

*Primary Examiner* — Gregory F Cunningham
(74) *Attorney, Agent, or Firm* — Nixon Peabody LLP; Linda B. Huber

(57) ABSTRACT

The present invention teaches systems and methods for a simple cardiac MRI approach that (1) continuously acquires data; (2) covers the entire heart with high isotropic resolution within a few minutes; and (3) requires no physiological gating and minimal user intervention. Applications of the inventive systems and methods include, but are in no way limited to cardiac cine, myocardial perfusion, coronary MRA, delayed enhancement imaging, myocardial T1-weighted imaging for fibrosis imaging, and myocardial T2-weighted imaging for edema imaging.

20 Claims, 16 Drawing Sheets

(51) Int. Cl.
   G01R 33/483   (2006.01)
   G01R 33/56    (2006.01)
   G01R 33/561   (2006.01)
   G01R 33/563   (2006.01)

(56) References Cited

PUBLICATIONS

Stehning, C. et al., Fast isotropic volumetric coronary MR angiography using free-breathing 3D radial balanced FFE acquisition, Magn Reson Med., 2004, 52:197-203.*

Amano et al., 'T2-Weighted Cardiac Magnetic Resonance Imaging of Edema in Myocardial Diseases', Scientific World Journal, vol. 2012, Article ID 194069, 7 pages, retrieved from Internet on Jan. 6, 2017 from <https://www.ncbi.nlm.nih.gov/pmc/articles/PMC3438740/pdf/TSWJ2012-194069.pdf>.*

Bhat, H. et al., 3D radial sampling and 3D affine transform-based respiratory motion correction technique for free-preathing whole-heart coronary MRA with 100% imaging efficiency, Magn Reson Med., 2011, 65(5):1-17.

Deshpande, V.S. et al, Reduction of transient signal oscillations in true FISP using a linear flip angle series magnetization preparation, Magn Reson Med., 2003, 49:151-157.

Gerber, B.L. et al., Myocardial first-pass perfusion cardiovascular magnetic resonance: history, theory, and current state of the art, Journal of Cardiovascular Magnetic Resonance, 2008, pp. 1-18.

Griswold, M. et al., the use of an adaptive reconstruction for array coil sensitivity mapping and intensity normalization, In Proceedings of the 10th Annual Meeting of ISMRM, Honalulu, Hawaii, USA, 2002, Abstract 2410.

Kellman, P. et al., Cardiac imaging techniques for physicians: late enhancement, J Magn Reson Imaging, 2012, 36(3):1-32.

Lai, P. et al., A dual-projection respiratory self-gating technique for whole-heart coronary MRA, J. Magn Reson Imaging, 2008, 28(3):1-19.

Moon, J.C. et al., Myocardial T1 mapping and extracellular volume quantification: a Society for Cardiovascular Magnetic Resonance (SCMR) and CMR Working Group of the European Society of Cardiology consensus statement, J Cardiovasc Magn Reson., 2013,5:92, pp. 1-12.

Pang, J. et al., Whole-heart coronary MRA with 100% respiratory gating efficiency: self-navigated three-dimensional retrospective image-based motion correction (TRIM), Magn Reson Med., 2014;71:(1), pp. 1-18.

Piccini, D. et al., Spiral phyllotaxis: the natural way to construct a 3D radial trajectory in MRI, Magn Reson Med., 2011, 66:1049-1056.

Pipe, J.G. et al., Sampling density compensation in MRI: rationale and an iterative numerical solution, Magn Reson Med.,1999, 41:179-186.

Pruessmann, K.P. et al., Advances in sensitivity encoding with arbitrary k-space trajectories, Magn Reson Med., 2001, 46:638-651.

Shechter, G. et al., MR motion correction of 3D affine deformations. In proceedings of the 11th Annual Meeting of ISMRM, Toronto, Canada, 2003, p. 1054.

Stehning, C. et al., Free breathing whole heart coronary MRA with 3D radial SSFP and self navigated image reconstruction, Magn Reson Med, 2005, 54:476-480.

Walsh, D.O., Adaptive reconstruction of phased array MR imagery, Magn Reson Med, 2000, 43:682-690.

Wong, S.T.S. et al., A strategy for sampling on a sphere applied to 3D selective RF pulse design, Magn Reson Med., 1994, 32:778-784.

* cited by examiner

| Seg # - Rep # | 1-1 | 1-2 | 1-3 | 2-1 | 3-1 | 3-2 | 4-1 | ... |
|---|---|---|---|---|---|---|---|---|
| Heartbeat Index | HB #1 | HB #2 | HB #3 | HB #4 | HB #5 | HB #6 | HB #7 | ... |

NAV Position
x=rejected o=accepted

FIG. 4

METHOD AND SYSTEM FOR "PUSH-BUTTON" COMPREHENSIVE CARDIAC MR EXAMINATION USING CONTINUOUS SELF-GATED 3D RADIAL IMAGING

CROSS REFERENCE TO RELATED APPLICATIONS

This application claims priority under 35 U.S.C. §119(e) from U.S. Provisional Application No. 62/062,781 filed on Oct. 10, 2014, which is hereby incorporated herein by reference in its entirety.

STATEMENT REGARDING FEDERALLY SPONSORED RESEARCH OR DEVELOPMENT

This invention was made with government support under Grant No. EB002623 awarded by the National Institutes of Health. The government has certain rights in the invention.

FIELD OF THE INVENTION

The present invention generally relates to imaging methods, and especially cardiovascular imaging methods.

BACKGROUND

The following description includes information that may be useful in understanding the present invention. It is not an admission that any of the information provided herein is prior art or relevant to the presently claimed invention.

Cardiac MRI is considered to be the gold standard for measuring cardiac structures and evaluating the heart muscle for a wide variety of conditions. It has not gained wide acceptance due to technical difficulties, including obtaining an adequate signal for ECG gating, the length of time required for examination, and the need for an extended series of breath holds for the various acquisitions. There is a need in the art for technology that will allow for a high quality cardiac MRI study during free breathing and without requiring electrodes on the patient's chest.

SUMMARY OF THE INVENTION

In various embodiments, the invention teaches a method for performing magnetic resonance imaging (MRI) on a subject. In some embodiments, the method includes performing one or more of the following scans using an MRI machine: (a) a scout scan to determine the position of the subject's heart; (b) a stress perfusion MRI scan on the subject's heart; (c) a cine MRI scan on the subject's heart; (d) a rest perfusion MRI scan on the subject's heart; (e) a coronary MRA scan on the subject's heart; and (f) a delayed enhancement MRI scan on the subject's heart; wherein (i) one or more scan is performed by using a continuous three dimensional radial acquisition scheme that results in the acquisition of a free-breathing k-space dataset, and (ii) image reconstruction for one or more scan is performed using a constrained or compressed sensing scheme, and wherein the method does not require (1) ECG triggering, (2) breath-holding by the subject, or (3) the use of a diaphragm navigator. In some embodiments, the method further includes performing T2-weighted imaging for edema imaging of the subject's heart and/or performing T1-weighted imaging for fibrosis imaging of the subject's heart. In certain embodiments, the image reconstruction for one or more scans includes conjugate-gradient sensitivity encoding (CG-SENSE) reconstruction. In some embodiments, the method further includes correcting for the subject's motion during one or more scans by a method including: (1) segmenting an acquired free-breathing k-space data set into different respiratory bins using self-navigation; (2) using a single bin as a reference, estimating the respiratory motion of all other bins using image-based 3D affine registration; and (3) using estimated translation vectors and affine transform matrices to modify the k-space data and trajectory, thereby resulting in motion-corrected k-space data and trajectory. In some embodiments, the method further includes incorporating the resulting motion-corrected k-space data and trajectory into a CG-SENSE reconstruction framework. In certain embodiments, the method further includes performing sensitivity self-calibration by a method including: (1) reconstructing motion-corrected individual coil images by gridding; (2) calculating coil sensitivity maps by using the eigenvector of local signal covariance matrices as the estimate of the respective sensitivity values at a specific spatial location; and (3) averaging the local image covariance matrices over blocks of a predetermined size to suppress streaking artifacts. In some embodiments, the averaging operation is implemented in MATLAB using a graphical processing unit (GPU). In certain embodiments, the sensitivity encoding operation is performed using a gridding/regridding approach with a density compensation function (DCF) iteratively calculated from the k-space trajectory to compensate for sampling nonuniformity. In some embodiments, the method further includes preconditioning by density compensation to accelerate convergence of the CG iterations. In some embodiments, the method further includes introducing a contrast agent into the subject's vascular system prior to or during any of one or more of scans a-f. In some embodiments, the method further includes diagnosing the subject with the presence or absence of a cardiovascular disease or condition based upon one or more resulting images. In certain embodiments, the cardiovascular disease is atherosclerosis and/or cardiomyopathy. In some embodiments, the MRI machine is a 1.5T scanner or a 3T scanner.

In various embodiments, the invention teaches a magnetic resonance imaging system that includes (1) a magnet operable to provide a magnetic field; (2) a transmitter operable to transmit to a region within the magnetic field; (3) a receiver operable to receive a magnetic resonance signal from the region; and (4) a processor operable to control the transmitter and the receiver; wherein the processor is configured to direct the transmitter and receiver to execute a sequence, including (a) acquiring magnetic resonance data from a volume of interest (VOI) that includes all or a portion of the subject's heart according to the methods described above; and (b) generating one or more images using the image reconstruction scheme described in the methods above, wherein a processor of the MRI machine and/or a subsystem configured to function therewith are configured to generate one or more images based on the magnetic resonance data acquired.

In certain embodiments, the invention teaches a non-transitory machine-readable medium having machine executable instructions for causing one or more processors of an magnetic resonance imaging (MRI) machine, and/or a subsystem configured to function therewith, to execute a method, including: performing one or more of the following scans: (a) a scout scan to determine the position of a subject's heart; (b) a stress perfusion MRI scan on the subject's heart; (c) a cine MRI scan on the subject's heart; (d) a rest perfusion MRI scan on the subject's heart; (e) a coronary MRA scan on the subject's heart; and (f) a delayed enhancement MRI scan on the subject's heart; wherein (i) one or more scan is performed by using a continuous three dimensional radial acquisition scheme that results in the acquisition of a free-breathing k-space dataset, and (b) image reconstruction for one or more scan is performed using a constrained or compressed sensing scheme, and wherein the method does not require (1) ECG triggering, (2) breath-holding by the subject, or (3) the use of a diaphragm navigator. In certain embodiments, the method executed further includes performing T2-weighted imaging for edema imaging of the subject's heart and/or performing T1-weighted imaging for fibrosis imaging of the subject's heart. In some embodiments, the image reconstruction for one or more scans includes conjugate-gradient sensitivity encoding (CG-SENSE) reconstruction. In some embodiments, the method executed further includes correcting for the subject's motion during one or more scans by a method including: (1) segmenting an acquired free-breathing k-space data set into different respiratory bins using self-navigation; (2) using a single bin as a reference, estimating the respiratory motion of all other bins using image-based 3D affine registration; and (3) using estimated translation vectors and affine transform matrices to modify the k-space data and trajectory, thereby resulting in motion-corrected k-space data and trajectory. In certain embodiments, the executed method further includes incorporating the resulting motion-corrected k-space data and trajectory into a CG-SENSE reconstruction framework. In some embodiments, the method executed further includes performing sensitivity self-calibration by a method including: (1) reconstructing motion-corrected individual coil images by gridding; (2) calculating coil sensitivity maps by using the eigenvector of local signal covariance matrices as the estimate of the respective sensitivity values at a specific spatial location; and (3) averaging the local image covariance matrices over blocks of a predetermined size to suppress streaking artifacts.

BRIEF DESCRIPTION OF THE DRAWINGS

Exemplary embodiments are illustrated in the referenced figures. It is intended that the embodiments and figures disclosed herein are to be considered illustrative rather than restrictive.

FIG. 4 demonstrates, in accordance with an embodiment of the invention, schematics of data extraction. In this example, for the motion-free dataset, the extracted blocks will be 1-3, 2-1, 3-2, 4-1 . . . and for the motion-corrupted dataset the blocks will be 1-1, 2-1, 3-1, 4-1 . . . .

DESCRIPTION OF THE INVENTION

Figure 1:
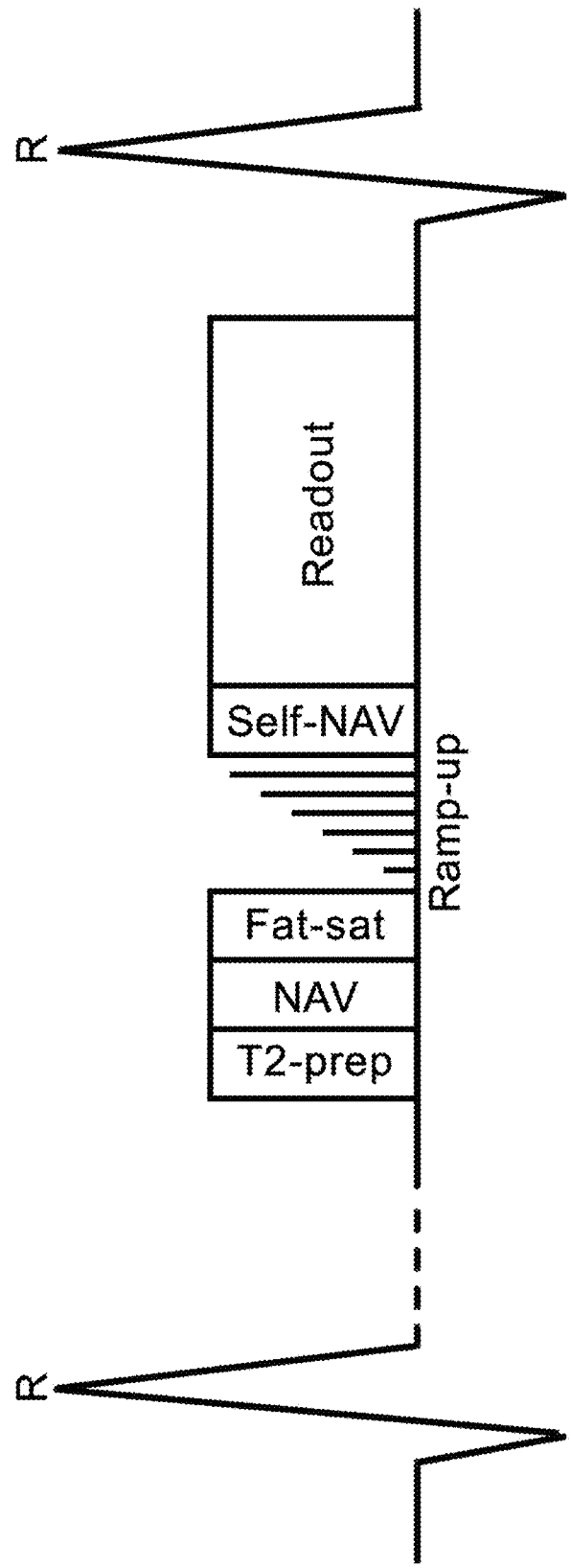
FIG. 1 demonstrates, in accordance with an embodiment of the invention, a schematic of a pulse sequence showing the acquisition scheme for one heartbeat. The ECG gated, free-breathing scan acquires the data during a total of ~500 heartbeats.

All references cited herein are incorporated by reference in their entirety as though fully set forth. Unless defined otherwise, technical and scientific terms used herein have the same meaning as commonly understood by one of ordinary skill in the art to which this invention belongs. Westbrook et al., *MRI in Practice* 4$^{th}$ ed., and Guyton and Hall, *Textbook of Medical Physiology* 12$^{th}$ ed., provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

"Conditions," "disease conditions," and "cardiovascular conditions," as used herein, may include but are in no way limited to atherosclerosis, cardiomyopathy, ischemic heart disease, arrhythmia, heart failure, and congenital heart disease.

"Mammal," as used herein, refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

By way of background, current cardiac MRI (CMR) techniques implemented on state-of-the-art MRI scanners require: (a) relatively long exam times, typically 60-90 minutes; (b) ECG gating (triggering); (c) multiple breath-holds; and (d) an expert operator. The long scan times are a particular hurdle for wide-spread adoption of CMR in clinical practice. Additionally, the need for accurate ECG gating reduces the image quality for certain patient populations (e.g., arrhythmic patients), and adds to the complexity of examination (e.g. preparation time and patient discomfort). A typical CMR exam currently requires 30 or more breath holds ranging from 5-50 seconds, which may be infeasible for some patients and add to the overall complexity of the exam.

Ultimately, all of the above require frequent interaction of an expert technologist. Such "operator dependency" of the image quality and need for a highly-trained technologist is a major shortcoming of current CMR methods and systems, and as indicated above has served as a significant obstacle to widespread adoption. Furthermore, clinically available methods typically suffer from non-isotropic spatial resolution, specifically poor resolution along the base-to-apex direction, which can be attributed to the use of 2D acquisition, as each slice can be typically imaged within the time constraint of a breath-hold.

Delayed enhancement has been shown to be an excellent method for defining scarring in the left ventricle, which is of great clinical importance in myocardial infarction and many forms of cardiomyopathy. Although laboratories and medical centers around the world are equipped to do these procedures, due to above-mentioned technical demands, there are relatively few imaging centers that offer the studies or that do them with significant volume.

As demonstrated in various embodiments described herein, the inventors have developed methods (including those implemented on various inventive systems described herein) in which MRI data is acquired using a 3D radial acquisition scheme continuously and without the need for ECG gating or breath holding. By employing advanced imaging reconstruction schemes ("constrained" or "compressed sensing" as described herein below), the inventive methods effectively accomplish cardiac "self-gating" (i.e., no need for ECG gating), correct for breathing motion, and achieve high image quality with isotropic 3D resolution. Due to the continuous un-interrupted acquisition with high gating efficiency (almost 100% of the data is accepted/used for reconstruction), the total scan time can be significantly reduced. As described herein in detail below, in some embodiments total scan time may be approximately 20-30 minutes.

The main challenge in using such image reconstruction schemes for 3D radial imaging is the very long image computation times needed. As used herein, the term "image computation time" refers to the time between the end of the MRI scan (acquisition of "raw data") and when the diagnostic-quality images are produced. Using conventional computing hardware platforms currently used in MRI scanners, this computation time may be as long as several hours.

In some embodiments of the present invention, an adjoining sub-system is used to "bypass" or complement the image-reconstruction engine of an MRI scanner. By way of additional background, in state-of-the-art MRI scanners, the acquired MRI raw data is sent to an image-reconstruction engine immediately following or during the acquisition of each MRI scan (either before or after digital storage of the data). This image-reconstruction engine can be either a separate computational "workstation" (provided by the MRI scanner vendor) or the same as the scanner's host computer (on which the MRI scan is prescribed by the operator/user).

In some embodiments of the present invention, using standard network connections, the raw data can be sent to one or more computational workstations (customized high-powered computational hardware) without disrupting the MRI scanner's default image-reconstruction engine, or, in alternative embodiments, the default engine (provided by the MRI scanner vendor) can be entirely disabled in favor of using one or more separate workstations. Then, the raw 3D radial MRI data can be processed using the developed image reconstruction methodology described herein (implemented as software on the above-described one or more workstations). Using the above-described computational hardware and software, the invention can reduce computation time to within a clinically-acceptable delay time of approximately 5 minutes or less.

Features/advantages of various embodiments of the present invention include, but are in no way limited to: (i) 3D radial acquisition as a "universal" acquisition scheme for cardiac MRI; (ii) continuous ungated acquisition without the need for ECG gating; (iii) cardiac and respiratory motion tracking/compensation with 100% efficiency, i.e., using all of the acquired raw data in the reconstruction process; (iv) highly accelerated reconstruction of undersampled data; (v) time-resolved imaging of cardiac, respiratory, and contrast dynamics in real-time; and (vi) combination of items (i)-(v) in a single cardiac imaging hardware/software tool for improved diagnostic imaging.

In some embodiments, the systems and methods described herein are implemented to perform non-ECG gated, free-breathing, 3D whole-heart myocardial perfusion quantification. In some embodiments, the systems and methods described herein are implemented to perform non-ECG gated, free-breathing, 3D whole-heart cine imaging. In some embodiments, the systems and methods described herein are implemented to perform non-ECG gated, free-breathing, 3D whole-heart coronary MRA. In some embodiments, the systems and methods described herein are implement to perform non-ECG gated, free-breathing, 3D whole-heart delayed enhancement imaging. In some embodiment, the systems and methods described herein are implemented to perform non-ECG gated, free-breathing, 3D whole-heart T1 mapping for fibrosis evaluation of a subject's cardiovascular system. In some embodiments, the systems and methods described herein are implemented to perform non-ECG gated, free-breathing, 3D whole-heart T2 mapping for edema imaging.

In some embodiments, a comprehensive, whole-heart cardiac MRI exam for a patient could be performed using the inventive systems and methods in 30 minutes or less, without ECG triggering, breath-hold, or navigator, according to the following sequence (or a variation thereof):
  Scout scan to determine the position of the heart (1 minute or less)
  T2-weighted imaging for edema imaging (5 minutes or less, optional)
  Stress perfusion (2 minutes or less)
  Cine MRI (5 minutes or less)
  Waiting time (5 minutes or less)
  Rest perfusion (2 minutes or less)
  Coronary MRA (5 minutes or less)
  Wait time (5 minutes or less)
  Delayed enhancement imaging (5 minutes or less)
  T1 mapping for fibrosis imaging (5 minutes or less, optional)

In certain embodiments, imaging is performed in 30 minutes or less. In some embodiments, all of the aforementioned imaging is performed in 40 minutes or less.

In various embodiments, magnetic resonance (MR) data acquisition for one or more of the scans described above can be accomplished using 3D radial sampling, as demonstrated and described in the examples set forth herein.

In certain embodiments of the above list of scans for a comprehensive MRI exam, the T2-weighted imaging for detection of edema uses a balanced steady state free precession (bSSFP) pulse sequence (3D radial trajectory either with or without T2 preparation, as described herein) that inherently achieves the T2 contrast needed to detect edema. In some embodiments, imaging parameters for the aforementioned bSSFP 3D radial pulse sequence are TR/TE=2.5-4.0/1.3-2.0 ms, flip angle=25°-55°, bandwidth=800-1200 Hz/pixel, FOV=$300^3$-$400^3$ mm$^3$, matrix size=$256^3$-$384^3$, total number lines=50,000-100,000. Additional background regarding bSSFP pulse sequence are provided in Pang et al. *Whole-heart coronary MRA with 100% respiratory gating efficiency: self-navigated three-dimensional retrospective image-based motion correction (TRIM)*. Magn Reson Med 2014; 71:67-74, which is hereby incorporated herein by reference in its entirety as though fully set forth.

In some embodiments, the stress/rest perfusion acquisition may use an RF-spoiled gradient-recalled echo sequence (3D radial trajectory with or without saturation-recovery preparation) that achieves T1-weighted imaging during the first-pass of the contrast agent. In some embodiments, imaging parameters for the T1-weighted 3D radial gradient-recalled echo sequence are: TR/TE=3.0-6.0/1.5-3.5 ms, flip angle=10°-25°, bandwidth=400-1200 Hz/pixel, FOV=$300^3$-$400^3$ mm$^3$, matrix size=$256^3$-$384^3$, and total number lines 50,000-100,000. (for additional details of standard T1-weighted first-pass stress/rest perfusion acquisition pulse sequence and saturation-recovery preparation see: Gerber et al. *Myocardial first-pass perfusion cardiovascular magnetic resonance: history, theory, and current state of the art.* Journal of Cardiovascular Magnetic Resonance 2008, 10:18 doi:10.1186/1532-429X-10-18, which is hereby incorporated herein by reference in its entirety as though fully set forth). Details of a similar gradient-recalled echo sequence using 3D radial trajectory have been provided in Pang et al. *ECG and navigator-free four-dimensional whole-heart coronary MRA for simultaneous visualization of cardiac anatomy and function*. Magn Reson Med. 2014 Sep. 12. doi: 10.1002/mrm.25450. [Epub ahead of print], PubMed PMID: 25216287, which is hereby incorporated herein by reference in its entirety as though fully set firth. Cine MRI for assessment of myocardial function and coronary MRA may be acquired using either a bSSFP 3D radial pulse sequence (as in Pang et al. Magn Reson Med 2014; 71:67-74, which is hereby incorporated herein by reference in its entirety as though fully set forth) or a gradient-recalled echo 3D radial pulse sequence (as in Pang, et al. "High-resolution whole-heart contrast-enhanced coronary MRA in 5 minutes with self-navigation and 100% gating efficiency." Journal of Cardiovascular Magnetic Resonance 2014; 16(Suppl. 1): O80. doi: 10.1186/1532-429X-16-S1-O80, which is hereby incorporated herein by reference in its entirety as though fully set forth). In some embodiments, when a bSSFP 3D radial pulse sequence is used for Cine MRI, the imaging parameters are TR/TE=2.5-4.0/1.3-2.0 ms, flip angle=25°-55°, bandwidth=800-1200 Hz/pixel, FOV=$300^3$-$400^3$ mm$^3$, matrix size=$256^3$-$384^3$, and total number lines=50,000-100,000. In some embodiments, when a gradient-recalled echo 3D radial pulse sequence is used for Cine MRI, the imaging parameters are TR/TE=3.0-6.0/1.5-3.5 ms, flip angle=5°-25° bandwidth=400-1200 Hz/pixel, FOV=$300^3$-$400^3$ mm$^3$, matrix size=$256^3$-$384^3$, total number lines=50,000-100,000.

In some embodiments, delayed enhancement imaging (also referred to as late-Gadolinium enhancement imaging)

and T1 mapping are both acquired using either of the before-mentioned bSSFP 3D radial or gradient-recalled echo 3D radial pulse sequences. For additional details regarding standard delayed-enhancement imaging, see: Kellman P and Arai A E, *Cardiac imaging techniques for physicians: late enhancement*, J Magn Reson Imaging. 2012 September; 36(3):529-42). For additional details regarding standard T1 mapping acquisitions see: Moon J C et al., *Myocardial T1 mapping and extracellular volume quantification: a Society for Cardiovascular Magnetic Resonance (SCMR) and CMR Working Group of the European Society of Cardiology consensus statement*, J Cardiovasc Magn Reson. 2013 Oct. 14; 15:92. doi: 10.1186/1532-429X-15-92. Both of these references are hereby incorporated herein by reference in their entirety as though fully set forth. In some embodiments in which a 1.5T MRI scanner is used, Cine MRI, coronary MRA, delayed enhancement, and T1 mapping acquisitions use a bSSFP 3D radial pulse sequence. In some embodiments in which a 3T MRI scanner is used, Cine MRI, coronary MRA, delayed enhancement, and T1 mapping acquisitions use a gradient-recalled echo 3D radial pulse sequence.

In some embodiments, image reconstruction is performed for one or more of the scans described above using "constrained" or "compressed sensing." In some embodiments, a conjugate-gradient (CG)-SENSE reconstruction scheme is used in conjunction with one or more of the scans described above, as illustrated in greater detail in the examples set forth herein. In various embodiments, Three-Dimensional (3D) Retrospective Image-Based Motion Correction (TRIM) is implemented to correct for patient motion that occurs during the data acquisition phase of one or more of the scans, as described in greater detail in the examples set forth herein.

In various embodiments, the scanning described herein is performed on a 1.5T MRI scanner. In some embodiments, the scanning described herein is performed on a 3T MRI scanner.

Figure 15:
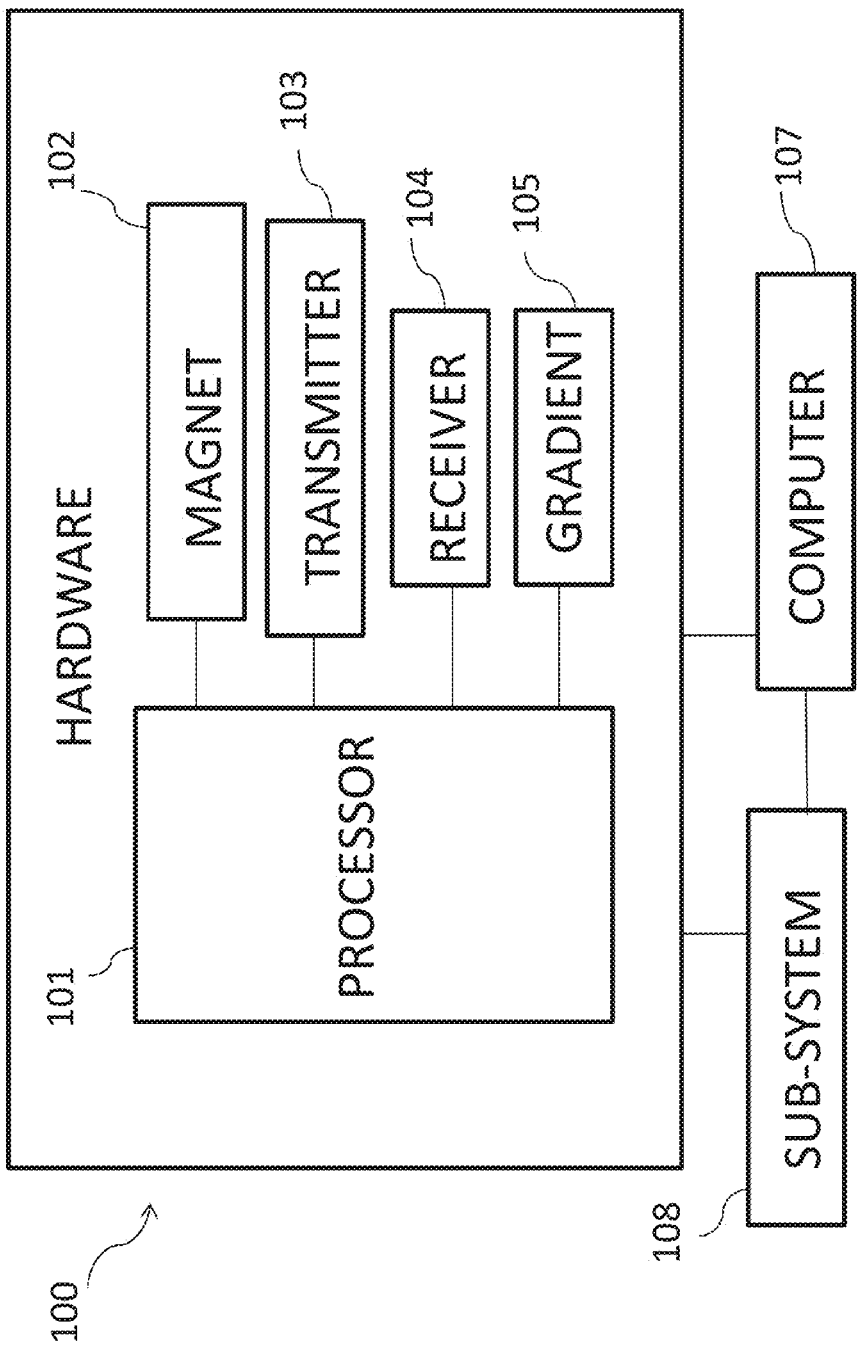
FIG. 15 depicts a system in accordance with an embodiment of the invention.

One of skill in the art would also readily appreciate that several different types of imaging systems could be used to perform the inventive methods described herein. Merely by way of example, the imaging systems described in the examples could be used. FIG. 15 also depicts a view of a system 100 that can be used to accomplish the inventive methods. System 100 includes hardware 106 and computer 107. Hardware 106 includes magnet 102, transmitter 103, receiver 104, and gradient 105, all of which are in communication with processor 101. Magnet 102 can include a permanent magnet, a superconducting magnet, or other type of magnet. Transmitter 103 along with receiver 104, are part of the RF system. Transmitter 103 can represent a radio frequency transmitter, a power amplifier, and an antenna (or coil). Receiver 104, as denoted in the figure, can represent a receiver antenna (or coil) and an amplifier. In the example shown, transmitter 103 and receiver 104 are separately represented, however, in one example, transmitter 103 and receiver 104 can share a common coil. Hardware 106 includes gradient 105. Gradient 105 can represent one or more coils used to apply a gradient for localization.

Processor 101, in communication with various elements of hardware 106, includes one or more processors configured to implement a set of instructions corresponding to any of the methods disclosed herein. Processor 101 can be configured to implement a set of instructions (stored in memory of hardware 106 or sub-system 108) to provide RF excitation and gradients and receive magnetic resonance data from a volume of interest. Sub-system 108 can include hardware and software capable of facilitating the processing of data generated by hardware 106, in conjunction with, or as a substitute for, the processing associated with image reconstruction that is normally handled by processor 101 in an MRI machine. One of skill in the art would readily appreciate that certain components of the imaging systems described herein, including the processor 101 and/or sub-system 108, are used to execute instructions embedded on a computer readable medium to implement the inventive data acquisition and image reconstruction methods described herein.

In some embodiments, computer 107 is operably coupled to hardware 106 and sub-system 108. Computer 107 can include one or more of a desktop computer, a workstation, a server, or a laptop computer. In one example, computer 107 is user-operable and includes a display, a printer, a network interface or other hardware to enable an operator to control operation of the system 100.

In various embodiments, the invention further teaches a non-transitory machine-readable medium having machine executable instructions for causing one or more processors of an MRI machine (such as those described herein) and/or a subsystem (supplementary computing station, as described herein) to execute a method, including (1) applying the MR pulse sequence of any of the preceding or ensuing embodiments to a volume of interest (VOI) in a subject, wherein the VOI includes a region of the subject's heart or the entirety of a subject's heart; (2) acquiring MR data from the volume of interest (VOI) in the subject; and (3) generating one or more images based on the magnetic resonance data using an image generating (reconstruction) technique described herein. In some embodiments, the non-transitory machine-readable medium has computer executable instructions for performing one or more of a series of scans (as described above), or optionally a comprehensive series of all of the scans describe herein.

In some embodiments, the invention includes using any of the methods or systems described herein to diagnose a subject with the presence or absence of a cardiovascular disease or condition, based upon the images acquired.

One skilled in the art will recognize many methods and materials similar or equivalent to those described herein, which could be used in the practice of the present invention. Indeed, the present invention is in no way limited to the methods and materials described.

EXAMPLES

Example 1

Whole-Heart Coronary MRA with 100% Respiratory Gating Efficiency: Self-Navigated Three-Dimensional Retrospective Image-Based Motion Correction (TRIM)

Self-Navigation

The pulse sequence is modified to include two additional readouts in the SI direction immediately before the imaging readouts (FIG. 1). With nonselective excitation associated with the 3D projection reconstruction trajectory, the Fourier transform of these lines represent the one-dimensional Radon transforms (i.e., one-dimensional projection) of the entire image volume. An anterior-posterior (AP) dephasing gradient is added to the second readout to suppress chest wall signal (For additional background see Lai et al. *A dual-projection respiratory self-gating technique for whole-heart coronary MRA*, Magn Reson Imaging 2008; 28:612-

620, which is hereby incorporated herein by reference in its entirety as though fully set forth).

Averaging of the two k-space lines creates a sinusoidal modulation of the underlying imaging volume. The following equation shows the calculation of the SI profile P(z) and describes the modulation effect from averaging:

$$P(z) = \frac{\int FOV\, c(r)\rho(r)dxdy + \int FOV\, c(r)\rho(r)e^{i\gamma G_{AP} y \Delta t_{AP}} dxdy}{2}$$

$$= \int FOV\, c(r)\rho(r)\cos\left(\frac{1}{2}\gamma G_{AP} y \Delta t_{AP}\right) e^{i\gamma G_{AP} \frac{y}{2} \Delta t_{AP}} dxdy$$

[EQUATION 1]

where x, y, and z are left-right, AP and SI directions, respectively, ρ(x, y, z) and c(x, y, z) are magnetization distribution and coil sensitivity, respectively, γ is the gyromagnetic ratio, $G_{AP}$ and $\Delta t_{AP}$ are the amplitude and duration of the AP dephasing gradient, respectively. Combined with an appropriate choice of the AP dephasing gradient strength, the chest wall signal is effectively suppressed to improve motion detection (Eq. [1]). In addition, only chest coils are used to minimize signal from the hack, which is also static.

Respiratory Motion Detection

The SI translation of the heart is detected from the acquired SI projection profile using a cross-correlation based method. The image space profile is interpolated 8-fold to achieve subpixel resolution (~0.1 mm). The template is selected from a manually chosen end-expiratory line. The normalized cross-correlation between the template and every self-navigation profile is then calculated as follows:

$$C(u) = \frac{\sum_x [f_u - \bar{f}_u](T - \bar{T})}{\sigma_f(u)\sigma_T}$$

[EQUATION 2]

where f is the self-navigation profile, T is the template, and u is the translation. $\bar{f}_u$ and $\sigma_f(u)$ are the average value and standard deviation of the profile within the template window, respectively, and $\bar{T}$ and $\sigma_T$ are the corresponding average and standard deviation tier the template, respectively. The respiratory position d is then defined as the translation value (in pixels), which renders the largest normalized cross-correlation:

$$d = \operatorname{argmax}_{u \in R} C(u) \quad \text{[EQUATION 3]}$$

Figure 2:
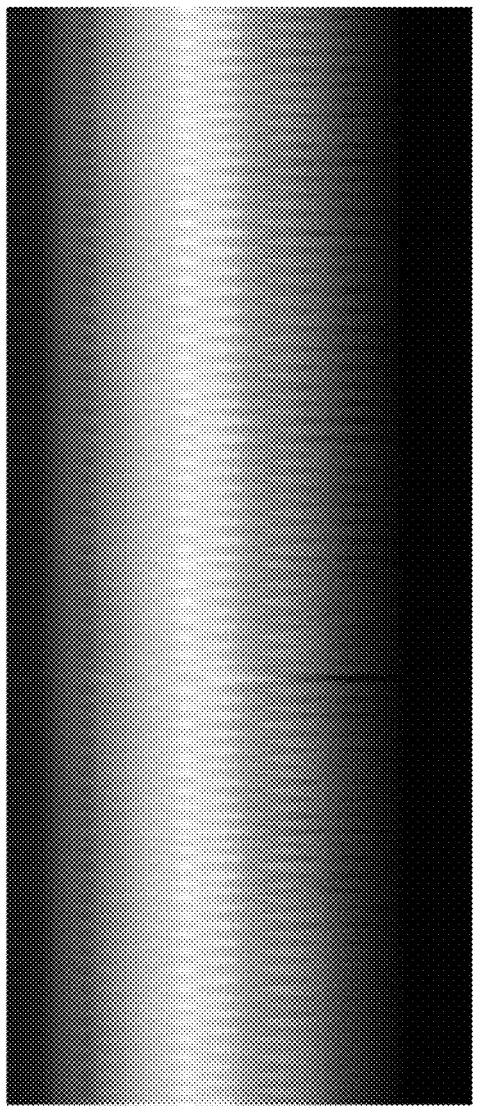
FIG. 2 demonstrates, in accordance with an embodiment of the invention: Top: time series of the self-navigation profiles. Bottom: detected superior-inferior (SI) motion of the heart.
Figure 2:
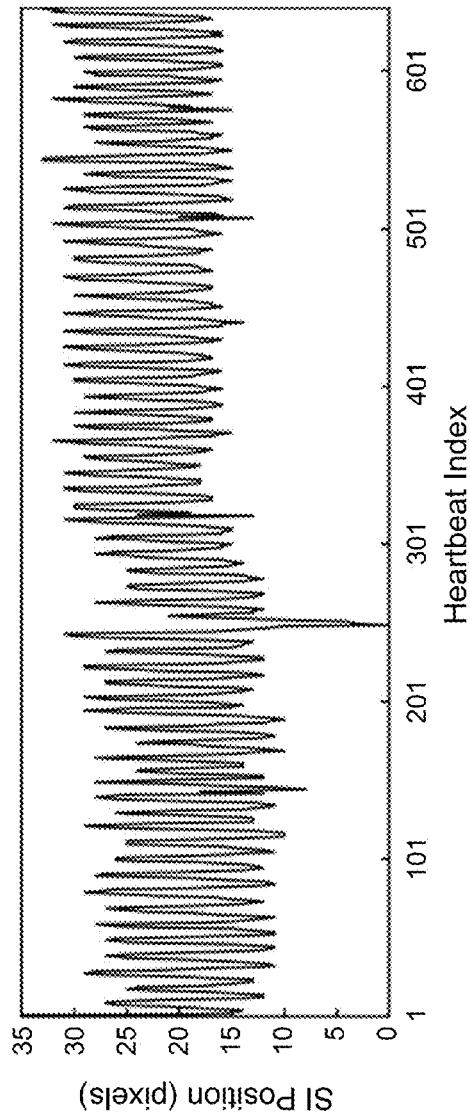

Example self-navigation profiles and the corresponding detected motion are shown in FIG. 2.

Motion Estimation and Correction

The various degrees of freedom of respiratory motion in cardiac imaging are not limited to rigid translations. A 3D affine transform, characterized by a linear transform of the coordinates and 3D translations, is a more realistic model for respiratory motion as it includes translation, rotation, scaling, and shearing. Therefore, it is used in some embodiments for motion estimation. Taking into account the static features in the imaged field of view (FOV) such as chest wall and spine, the motion estimation is performed after applying a 3D mask containing only the heart region. The motion estimation program is written in C using the Insight Toolkit, an open-source image processing toolkit (See Luis et al. *The ITK Software Guide*, 2$^{nd}$ ed. Updated for ITK version 2.4, 2005, which is incorporated by reference herein in its entirety as though fully set forth). Rather than prospectively rejecting any portion of the acquired data, all the k-space lines are segmented into six respiratory bins according to the corresponding respiratory positions hence achieving 100% scan efficiency (although six respiratory bins are used in this exemplary embodiment, one of skill in the art would readily appreciate that more or less bins could be used as well with similar results). From each bin, a low-resolution 3D image is reconstructed. As the k-space pattern in each bin is generally non-uniform and undersampled, straightforward regridding using the analytical 1/kr$^2$ density compensation will show a considerable amount of streaking artifacts. In some embodiments, to suppress these artifacts, a lowpass filter is computed adaptively based on the Nyquist radius of the undersampled k-space and is then applied to the k-space data before regridding. One of the six bins is identified as end-expiratory and the corresponding low-resolution image is set as the reference. The other five bins are then registered to the reference using the masked affine model, resulting in an affine matrix and a translation vector for each bin, which will be stored for subsequent motion correction, as described next.

Translations in image space correspond to linear phase modulations in k-space. In fact, a general affine transform of image space coordinates corresponds to an affine transform of k-space coordinates (See Shechter et al. *MR motion correction of 3D affine deformations*. In proceedings of the 11$^{th}$ Annual Meeting of ISMRM, Toronto, Canada, 2003. P. 1054., which is hereby incorporated herein by reference in its entirety as though fully set forth). Therefore, knowing the image-space transform parameters, motion correction can be directly conducted in k-space, without the need to grid the k-space data and perform time-consuming image space interpolation, as described in Bhat et al. *3D radial sampling and 3D affine transform-based respiratory motion correction technique for free-breathing whole-heart coronary MRA*. Magn. Reson Med 2011; 65:1269-1277 which is hereby incorporated herein by reference in its entirety as though fully set forth. The following equation describes the relation between the acquired and affine-motion-corrected datasets:

$$F'_n(k) = \frac{\exp(j2\pi(A_n^{-T} k^T b_n))}{|\det(A_n)|} F_n(A_n^{-T} k_n)$$

Figure 3A:
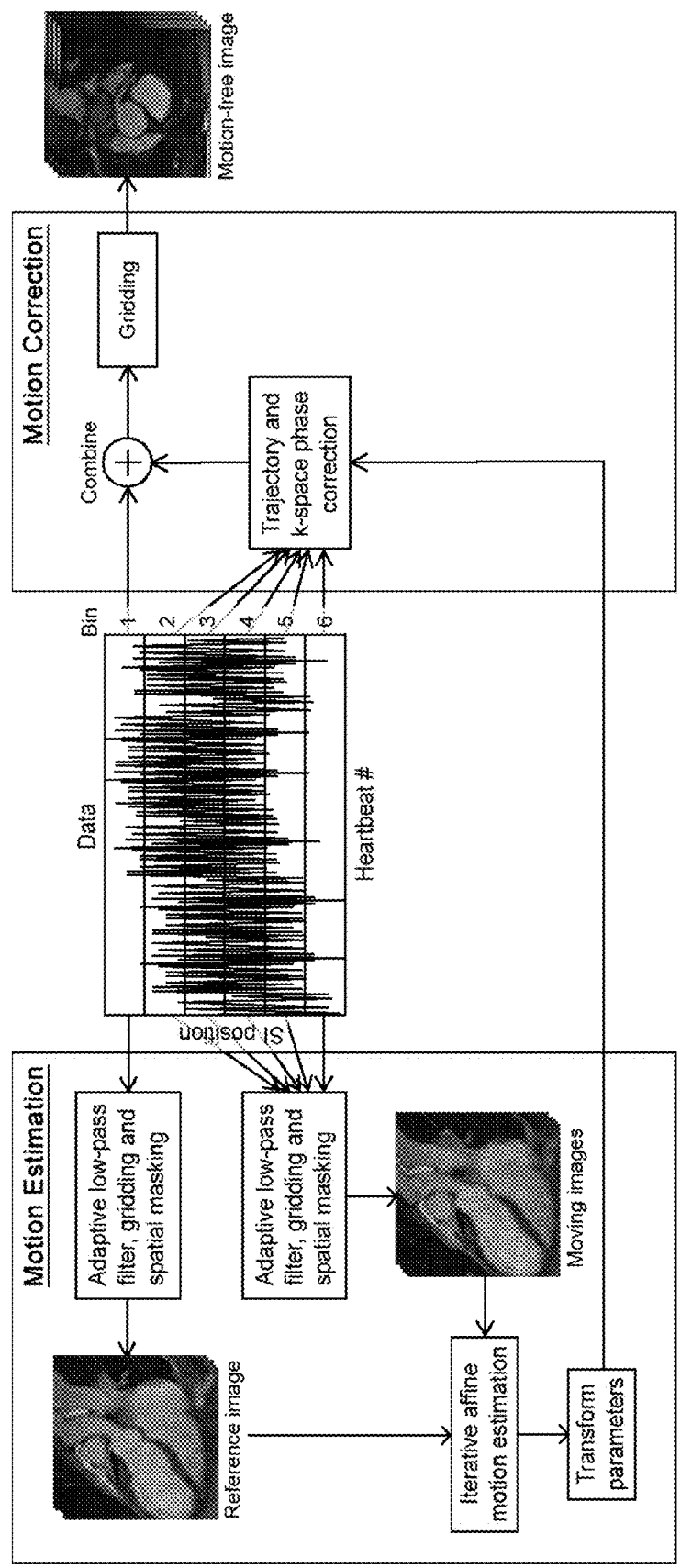
FIGS. 3A and 3B demonstrate, in accordance with an embodiment of the invention, schematics of the simultaneous cardiac and respiratory binning and the respiratory motion correction framework: the imaging data was mapped to different cardiac and respiratory bins based on its cardiac and respiratory phase derived from the self-gating signal. Next, with one common respiratory phase selected as reference (in this example, respiratory phase 1 for cardiac phases 1-9), all other bins (respiratory phases 2-6, cardiac phases 1-9) were registered to the corresponding reference bin of the same cardiac phase using an affine transform model. The k-space trajectory and data was then modified accordingly for respiratory motion correction. The 6 images on the left show the 6 respiratory phases in cardiac phase 1. The horizontal dashed lines help visualize the SI motion of the heart due to respiration. The 9 images on the bottom show the 9 cardiac phases in respiratory phase 6. The contraction of the left ventricle can be clearly seen.
Figure 3B:
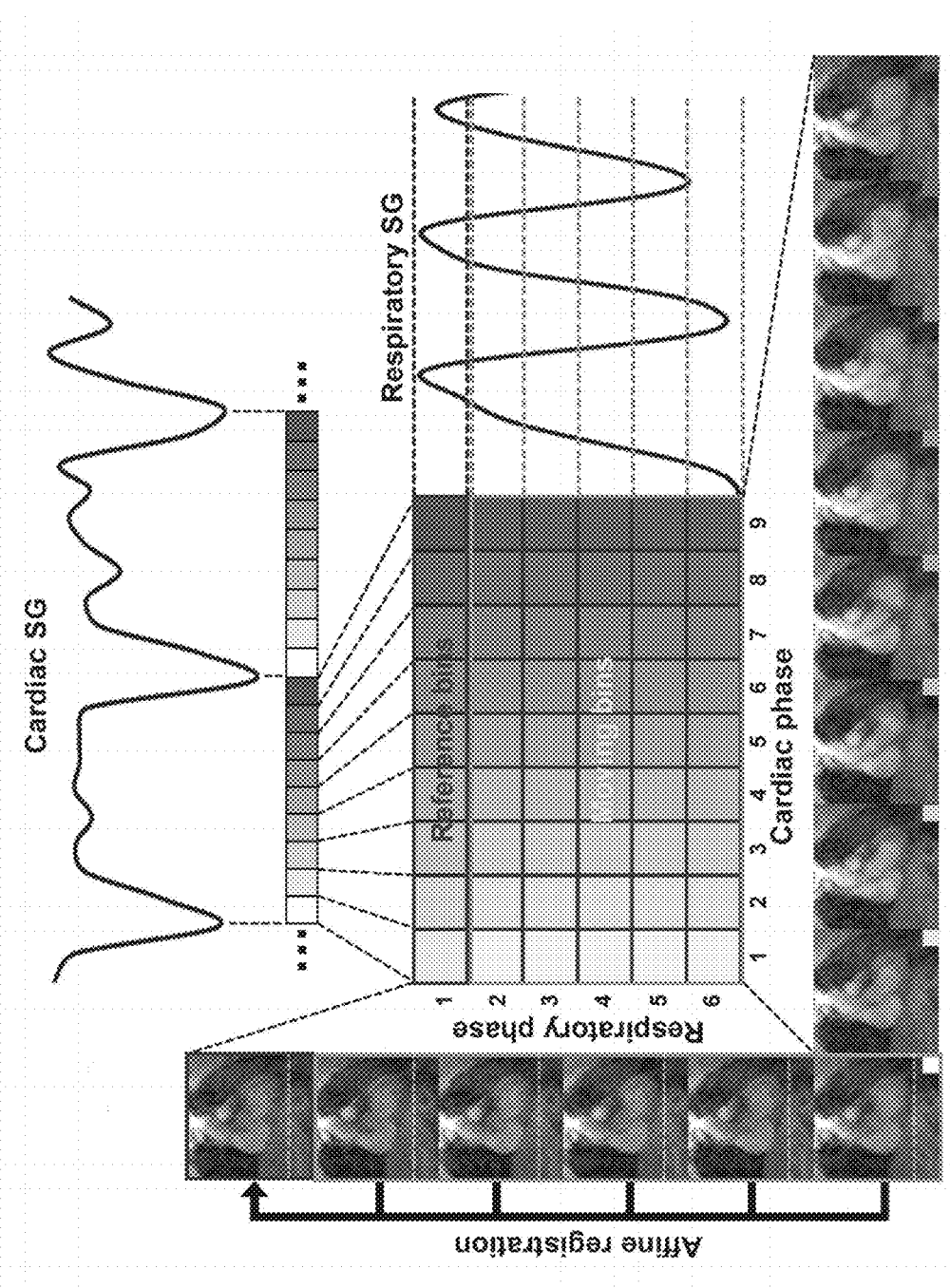

[EQUATION 4]

where $F_n(k)$ and $F'_n(k)$ are the acquired and corrected k-space for bin n, respectively, and $A_n$ and $b_n$ are the corresponding affine matrix and translation vector, respectively. The new k-space data and trajectory are fed into a regular regridding program to reconstruct the final motion corrected image. Compared with the image-domain registration method in Bhat et al. (See above) using Insight Toolkit, this approach is significantly faster (<1 min vs. 25 min, for a four-channel dataset). FIG. 3 summarizes the workflow of the method described in this section.

In Vivo Experiments

In vivo experiments were performed on clinical 1.5 T scanners (MAGNETOM Espree and Avanto, Siemens AG Healthcare, Erlangen, Germany) with institutional review board approval and written consent obtained before each exam. A 12-channel cardiac coil was used for data acquisition. Whole-heart coronary MRA images were acquired using an ECG-gated, T2-prepared, fat-saturated bSSFP sequence with a 3D radial trajectory (See Stehning et al. *Fast isotropic volumetric coronary MR angiography using free-breathing 3D radial balanced FFE acquisition.* Magn Reson Med 2004; 52:197-203, which is hereby incorporated herein by reference in its entirety as though fully set forth). The sequence was modified to include self-navigation readouts, while the diaphragm navigator module was kept for comparison purposes. The scan parameters were as follows: pulse repetition time/echo time=3.2 ms/1.6 ms, FOV=$260^3$-$300^3$ mm$^3$, matrix size=$256^3$, voxel size=1.0-1.2 mm$^3$ interpolated to 0.5-0.6 mm$^3$, 250 µs hard pulse with flip angle=90°, readout bandwidth=781 Hz/pixel, 15 preparation pulses in each heartbeat with linear flip angle modulation (For additional background see Deshpande et al. *Reduction of transient signal oscillations in true-FISP using a linear flip angle series magnetization preparation.* Magn Reson Med 2003; 49:151-157, which is hereby incorporated herein by reference in its entirety as though fully set forth), T2-prep duration=40 ms, chemically selective fat-saturation, 25-40 lines per heartbeat in data acquisition windows of 80-130 ms, 16,000 to 16,800 total projections. A four chamber cine scan was performed to determine the quiescent imaging window. To compare the inventive method with conventional navigator gating, a first group of five healthy volunteers (average age 26.7±3.0 years, 1 woman, 4 men) were scanned with the above sequence, and the acquisition was gated by respiratory navigator. From the raw dataset, a motion-free and a motion corrupted dataset were extracted as shown in FIG. 4. In the gated acquisition, each k-space segment was repeatedly acquired until the navigator position falls into the acceptance window. Therefore, the gated data was obtained by extracting the last repetition of each segment, and extracting the first repetitions generated a free-breathing, motion-corrupted data. This approach minimizes confounding factors such as patient movement and heart-rate variation between scans. Three 3D images were reconstructed for each subject: one from the prospectively gated data (Gated), one from the motion corrupted data without any correction (NC), and one from the motion corrupted data with the novel motion correction technique (TRIM). To further determine the performance of the inventive self-navigated technique, a second group of 12 healthy volunteers (average age 33±7.6 years, 3 women, 9 men) were scanned. Specifically, the new technique was compared with the previous navigator-based binning method that uses the same pulse sequence. Both diaphragm navigator and self-navigation data were collected, but the acquisition was not gated. By this what is meant is, self-navigation was compared with diaphragm navigator as a data binning method, with the same k-space sampling strategy (See Bhat et al. as above). Three 3D images were reconstructed from a raw dataset: without correction (NC), corrected with navigator binning (NAV-bin), and one with the inventive technique (TRIM). Image reconstruction was performed offline using MATLAB (Mathworks, Natick, Mass.) with parallel computing toolbox on a Dell Precision T7500 workstation. All images were reformatted using CoronaViz software (Siemens Corporate Research, Princeton, N.J.). Quantitative measurement of left anterior descending artery (LAD), left circumflex artery (LCX), and right coronary artery (RCA) length and sharpness were performed automatically using the same software. Qualitative image scoring was also performed by two independent and experienced readers that were blinded to different techniques on a five-point scale (0-4): 0, no coronary arteries are visible, 1, coronary arteries are visible but of non-diagnostic quality; 2, coronary arteries are of diagnostic quality but very blurred; 3, coronary arteries are of diagnostic quality and slightly blurred; 4, excellent image quality with minimal to no blurring.

Results

Figure 5:
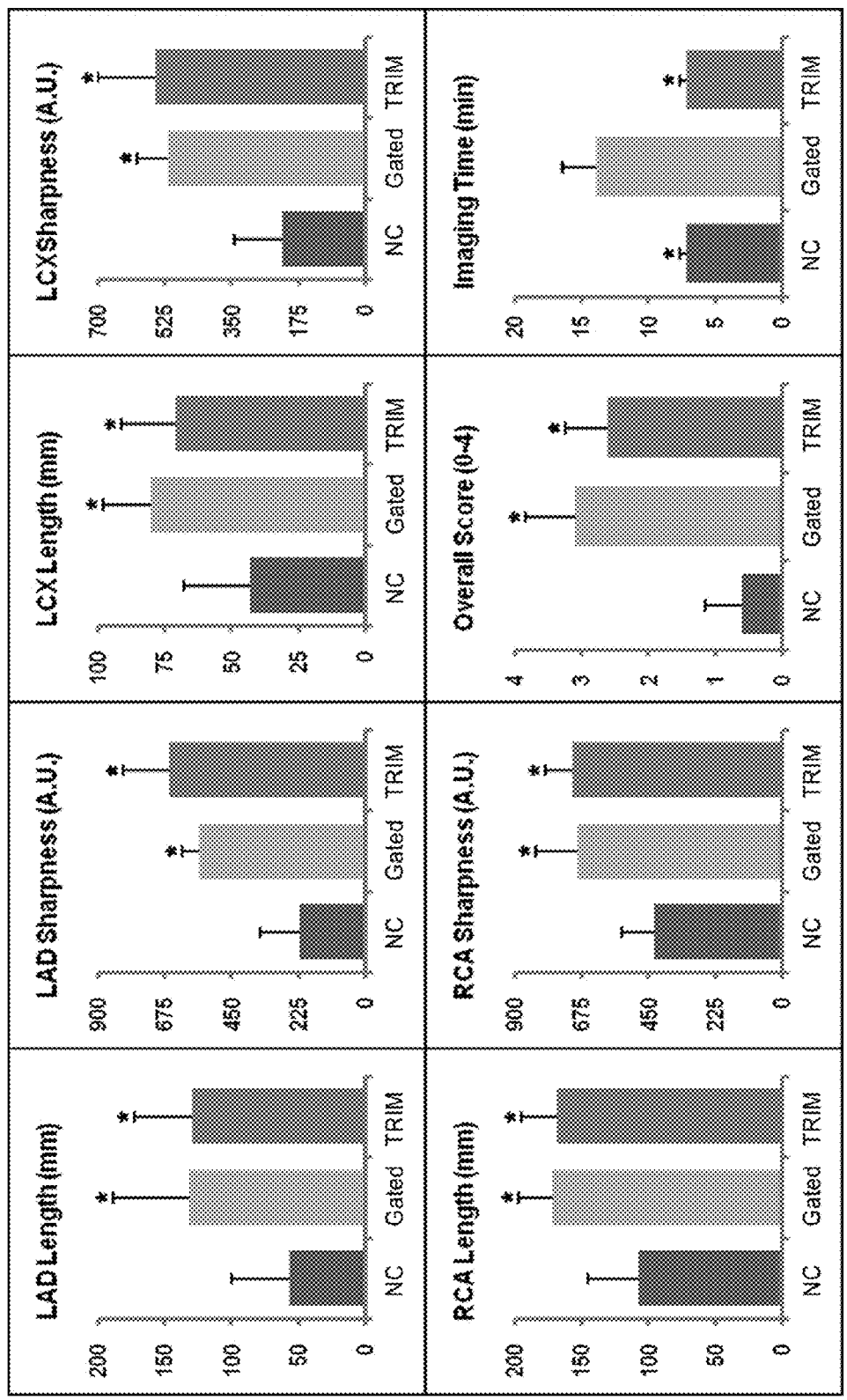
FIG. 5 demonstrates, in accordance with an embodiment of the invention, comparisons of the performance of NC, Gated, and TRIM (*P<0.05).

For the comparison between NC, Gated, and TRIM, both Gated and TRIM showed better (P<0.05) image qualities than NC in terms of qualitative scores and LAD, LCX, and RCA length and sharpness. No significant differences were found between Gated and TRIM in both qualitative and quantitative evaluations. Notably, imaging time with TRIM (7.1±0.5 min) was significantly shorter than that using Gated (13.9±2.6 min) due to 100% gating efficiency (P<0.05). Results are summarized in FIG. 5.

Figure 6:
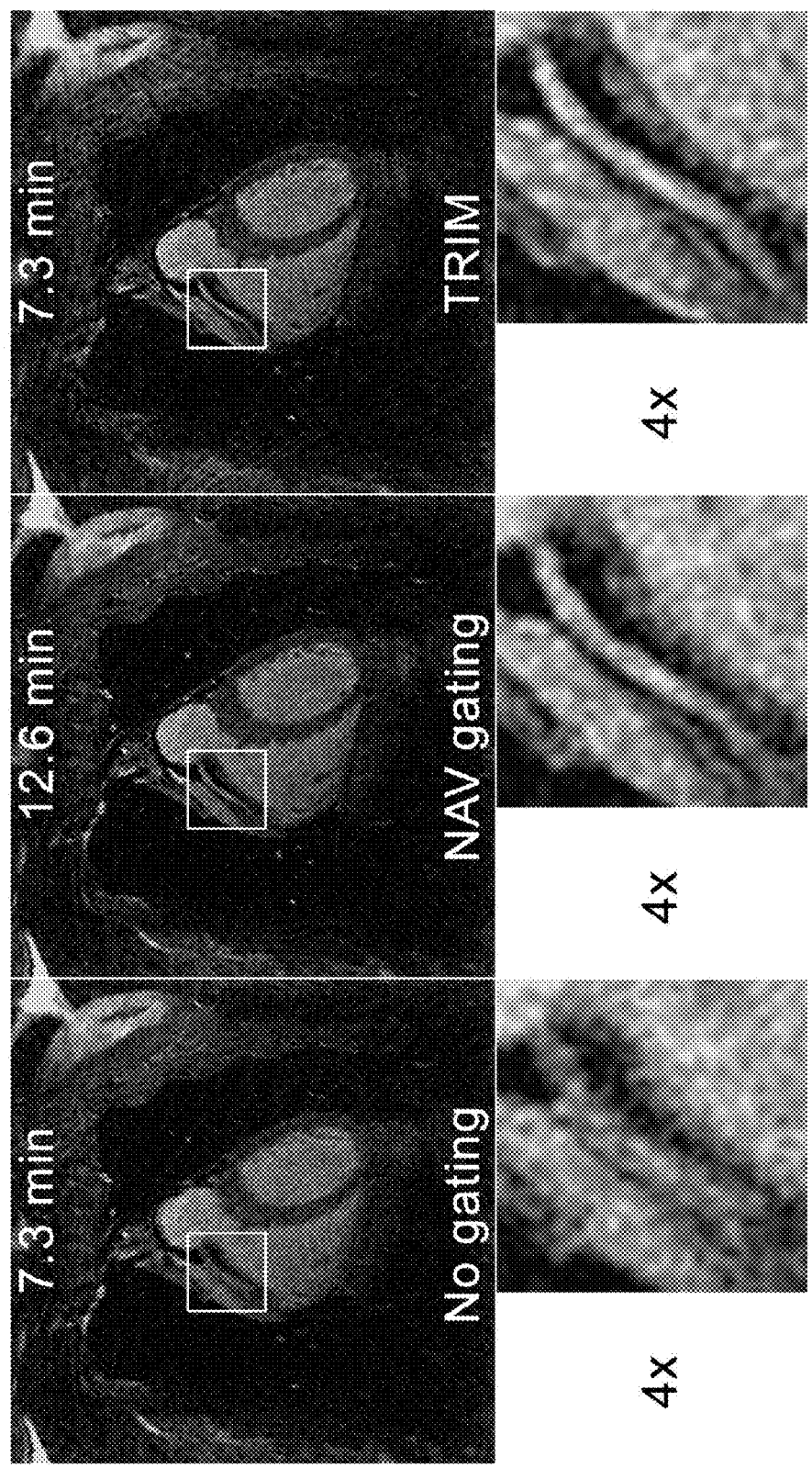
FIG. 6 demonstrates, in accordance with an embodiment of the invention, comparison of ungated and uncorrected image (left), image with conventional navigator gating (middle) and with an innovative motion correction method (right). As can be seen, the innovative method delivers excellent image quality without the penalty in scan time.

FIG. 6 shows a coronal slice as an example comparison between NC, Gated, and TRIM. Without any motion correction, the image is blurry and has poor visualization of the example RCA segment. The navigator gated image shows good image quality at a cost of a significantly longer scan time. With imaging time the same as the ungated one, the inventive method significantly reduces motion blurring and yields excellent coronary artery visualization.

Figure 7:
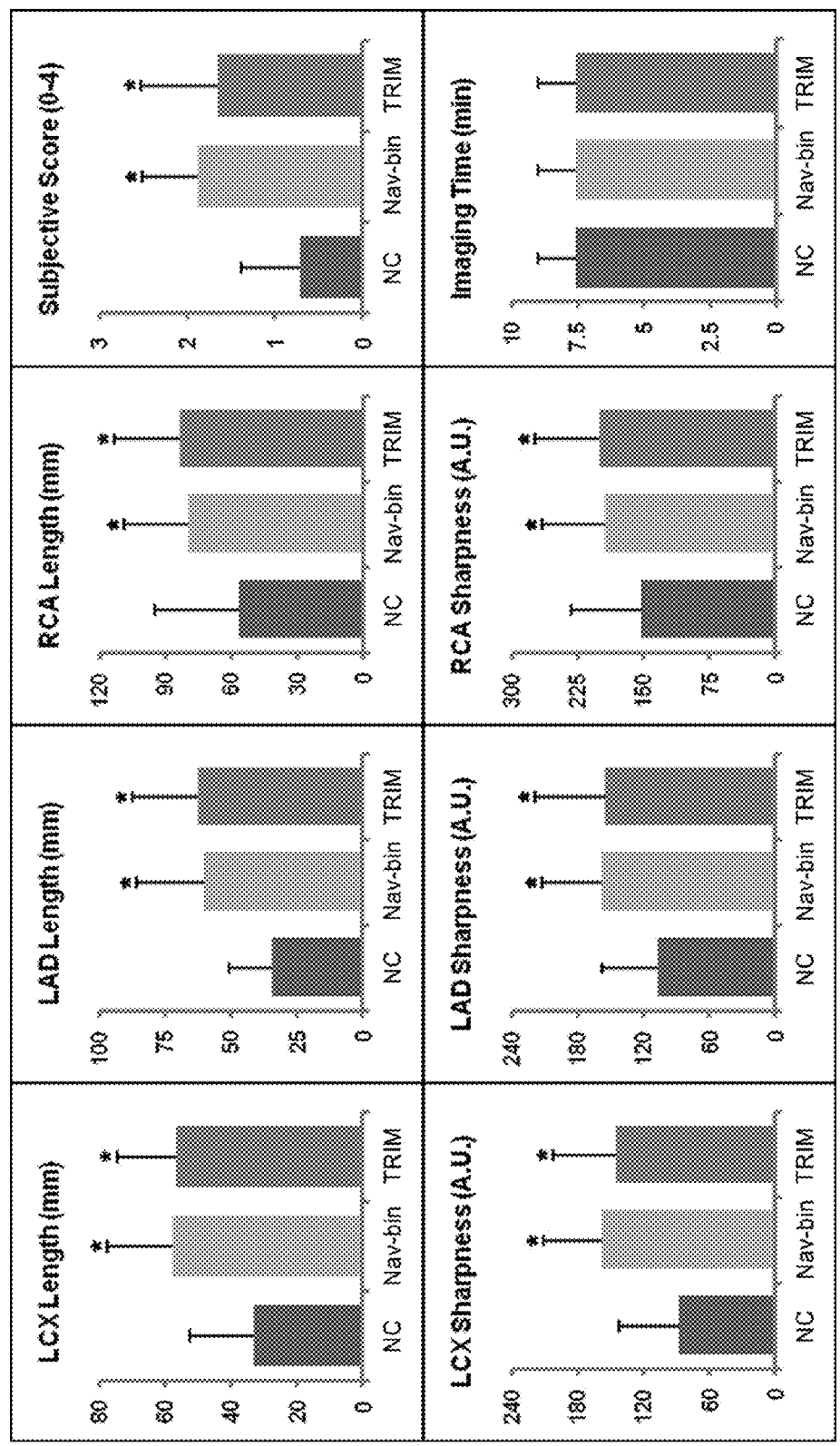
FIG. 7 demonstrates, in accordance with an embodiment of the invention, comparisons of the performance of NC, NAV-bin, and TRIM (*P<0.05).

For the comparison between NC; NAV-bin, and TRIM, both NAV-bin and TRIM had better (P<0.05) image qualities than NC in terms of qualitative scores and LAD, LCX, and RCA length and sharpness. In addition, no significant differences in image qualities were found between NAV-bin and TRIM. The scan time is 7.67±1.5 min. for all three methods. Results are summarized in FIG. 7.

Figure 8:
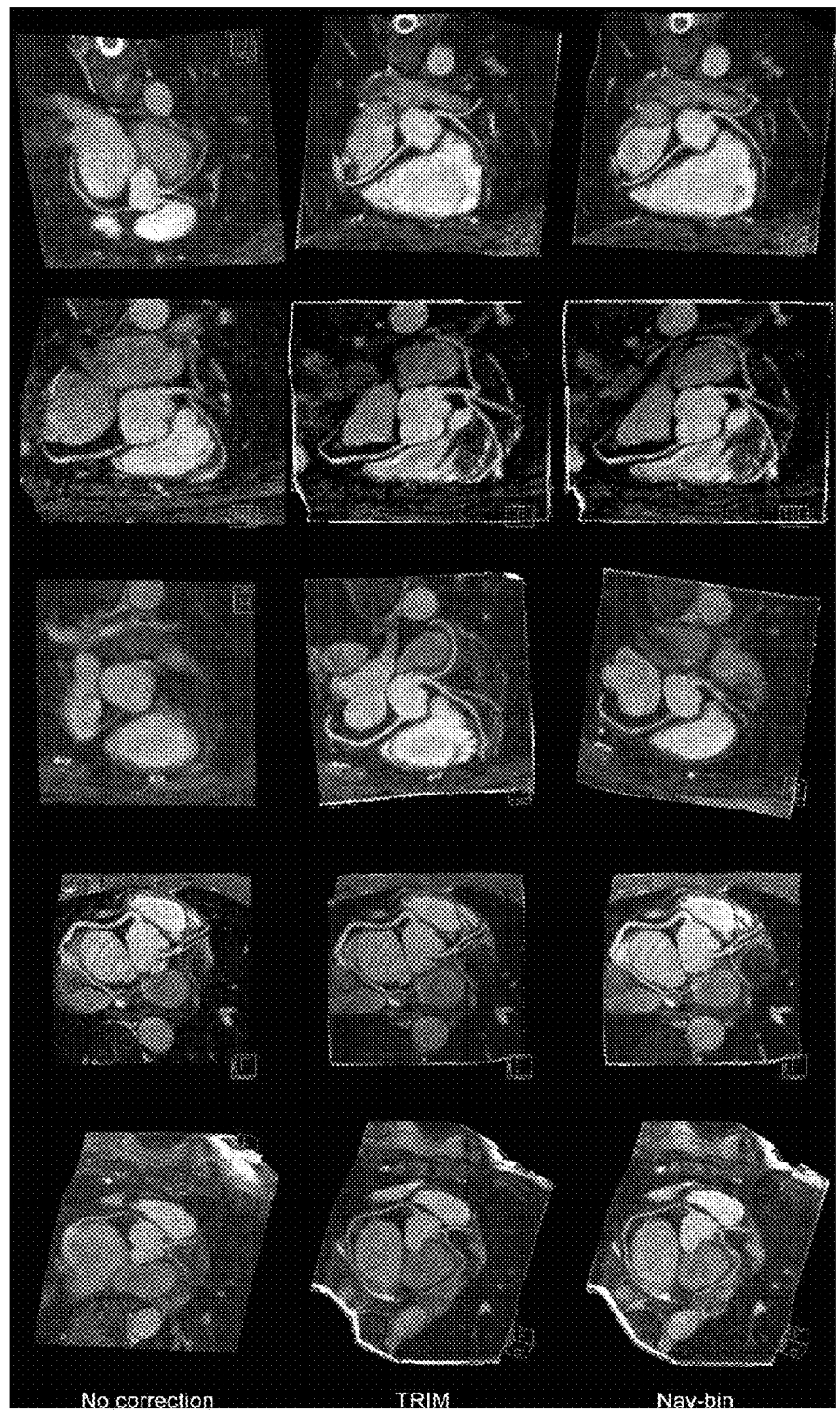
FIG. 8 demonstrates, in accordance with an embodiment of the invention, comparison of the reformatted images: no correction (left), TRIM (middle), NAV-bin (right). As can be seen TRIM delivers excellent image quality without the need for a diaphragm navigator.

FIG. 8 shows reformatted coronary artery images from five healthy subjects comparing NC, NAV-bin, and TRIM. Without any motion correction (first column), the images are blurry and have poor visualization of the coronary arteries. With imaging time unchanged and without the need to set up a navigator, the inventive motion correction technique (second column) significantly reduces motion blurring and shows excellent coronary artery visualization. The navigator binning approach (third column) shows similar improvements.

Discussion

Presented in this section is a retrospective image based respiratory motion correction method with self-navigation for whole-heart coronary MRA. The self-navigation signal is used to segment k-space data into different respiratory bins, facilitating affine motion estimation of the moving bins with respect to a selected reference bin. The motion correction is conducted very efficiently by modifying k-space phase and trajectory, and the final image is reconstructed by regridding the motion-corrected data.

The method provides a number of advantages compared with previous approaches. First, prescribing the diaphragm navigator requires additional time to perform multiple scout scans to position the crossed pair of slices onto RHD. The time-consuming procedure complicates the setup process of coronary MRA protocols and requires specialized operator expertise. Therefore, compared with techniques that require navigators, using self-navigation will save a significant amount of scanner time and make whole-heart coronary MRA protocols much more user friendly. Second, the scan duration with navigator gating is usually significantly prolonged and unpredictable, due to the fact that the scan efficiency (ratio between accepted and total acquired data) is usually low (around 40%) and highly dependent on the subject's breathing pattern. In addition, especially low navigator efficiency usually indicates an unsuccessful scan. By accepting all free-breathing data and performing retrospective binning and image-based motion correction, the inventive method is able to make the scan time both shorter and less variable, which reduces subject discomfort, and in turn the chances of bulk motion and respiratory pattern drift, thus improving the robustness of coronary MRA, Third, the inventive method performs motion correction using an affine transform, which better characterizes the respiratory motion than translation-only models. This is especially necessary for larger acceptance windows, Finally, it has been shown that there can be a hysteresis between diaphragm and heart motion, resulting in inaccurate motion detection with the diaphragm navigator. Although not shown in this study, self-navigation can avoid this potential error by directly tracking heart position. On healthy volunteers, the method described in this section was able to provide excellent coronary artery delineation and 1 mm isotropic spatial resolution with a scan time of around 7 min, or 500 heartbeats.

Figure 9:
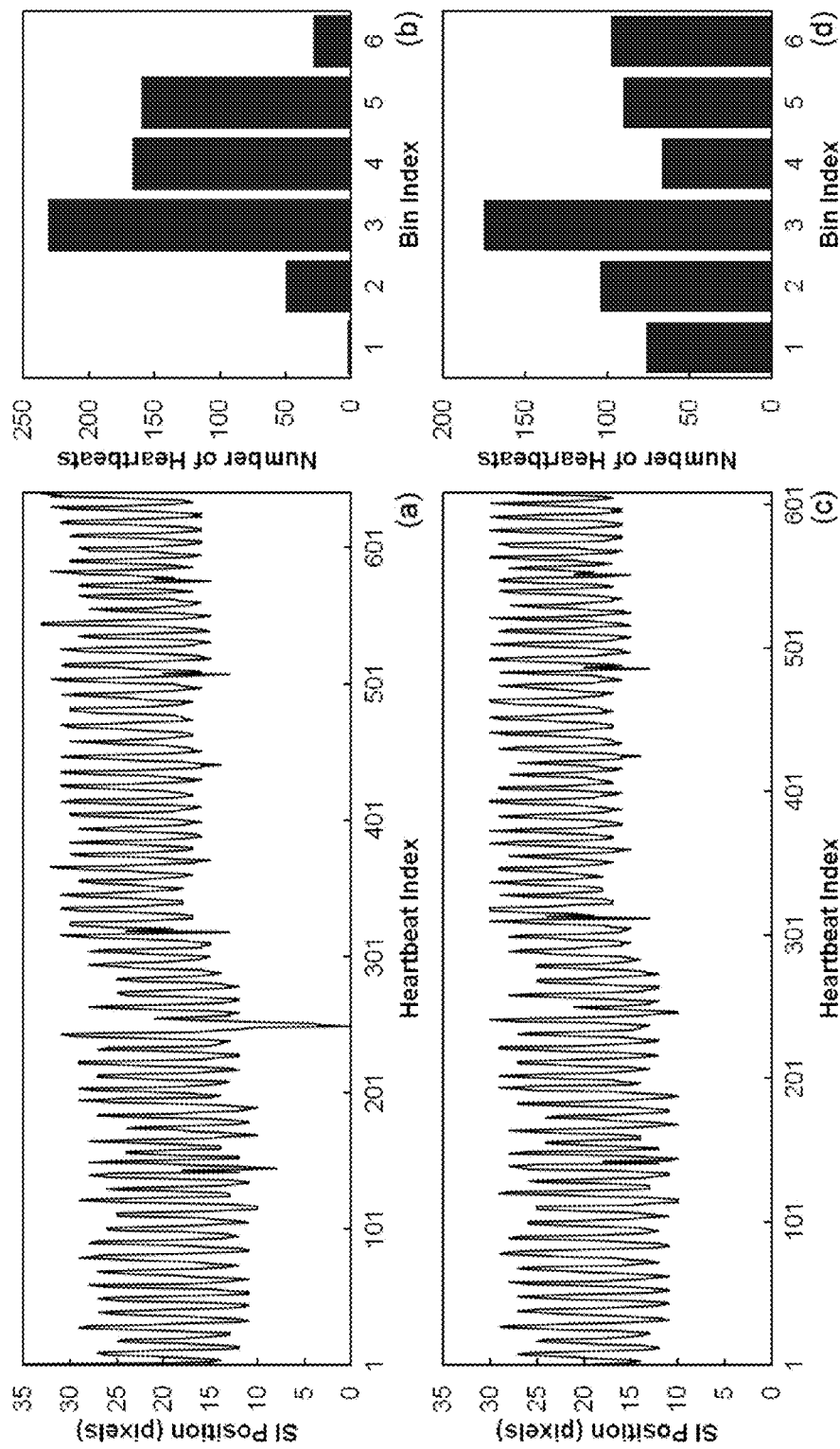
FIG. 9 demonstrates, in accordance with an embodiment of the invention, the effect of outlier respiratory positions on binning. In this example, the original respiratory pattern (a) has outlier positions around the 250th heartbeat. The corresponding binning result (b) has bin 1 and bin 6 with an insufficient number of heartbeats. The processed respiratory pattern (c) with the outliers discarded results in a more uniform binning result (d) that allows subsequent accurate motion estimation.

Importantly, Bhat et al, (see above) concluded by simulation that ~40 heart beats are needed in each bin to guarantee accurate motion estimation. This is often violated for subjects with irregular breathing patterns. For example, as shown in FIG. 9, outlier respiratory positions will result in some bins having too few projections to reconstruct an adequate image fir motion estimation. Currently, if a first binning results in one or more bins with insufficient number of projections, the data corresponding to the outliers (defined as more than two standard deviations away from the median) are discarded, and the remaining data is reprocessed. For subjects with very deep breathing, using a fixed number of bins may result in a good amount of residual intra-bin motion. In some embodiments, the number of bins, as well as the size and position of each individual bin may be adaptively determined to better segment k-space data; hence, trading between the accuracy of motion estimation, which corresponds to the amount of data in one bin, and residual motion, which corresponds to bin size.

Moreover, it is shown that for some subjects there is a hysteresis between RHD and heart position, therefore a particular diaphragm position may correspond to two different heart positions and shapes for inspiration/expiration. The method described in this section uses self-navigation to avoid this ambiguity but still assumes a one-to-one relationship between the SI heart translation and other motion parameters, such as AP and left-right translation. It has been shown that hysteresis can be present in between SI/AP or SI/left-right translations, which could be a potential source of residual motion artifacts in some subjects and needs further investigation.

Finally, the most time-consuming step in the reconstruction scheme described in this section is the 3D affine motion estimation with the Insight Toolkit software package. The motion estimation program uses a gradient descent algorithm that converges slowly especially when the motion is significant, e.g., for bins far away from the reference bin. It is possible to detect bulk translation parameters, in a beat-by-beat fashion, from self-navigation projections in one or more directions. Correcting for translations first will accelerate the iterative motion estimation process as the bins to be registered are now "closer" to the reference. This may also help in resolving some of the intra-bin translational motion, Conclusions In conclusion, certain aspects of the invention disclose a respiratory motion correction method for whole-heart coronary MRA combining self-navigation and image-based motion correction to achieve 100% gating efficiency, eliminating both the need of setting up a diaphragm navigator and gating the acquisition, hence provides a smooth workflow and enables high isotropic resolution (1 mm$^3$) and whole heart coverage in a short scan time (7 min). Excellent image quality was achieved in healthy volunteers.

Example 2

Methods II—Accelerated Whole-Heart Coronary MRA Using Motion-Corrected Sensitivity Encoding with Three-Dimensional Projection Reconstruction Motion-Corrected 3D Projection Reconstruction (3DPR) Sensitivity Encoding Several works have combined retrospective motion correction with sensitivity encoding in cardiac imaging applications. In this example, the inventors use a two-step procedure for the inventive motion-corrected conjugate gradient sensitivity encoding (CG-SENSE) reconstruction.

The first step follows the respiratory motion correction methods described above. With the cardiac motion suppressed by electrocardiograph (ECG) gating, the free-breathing dataset is segmented into different respiratory bins using self-navigation. With one bin being the reference, the respiratory motion of all other bins is estimated using image-based 3D affine registration, which has been shown to be a good approximation of the respiratory motion. Finally, the motion correction is accomplished by using the estimated translation vectors and affine transform matrices to modify the k-space data and trajectory.

In the second step, the motion-corrected k-space data and trajectory is incorporated into the CG-SENSE reconstruction framework. For additional background, see Pruessmann et al. *Advances in sensitivity encoding with arbitrary k-space trajectories*, Magn Reson Med 2001; 46:638-651, which is hereby incorporated herein by reference in its entirety as though fully set forth. For sensitivity self-calibration, the motion-corrected individual coil images are reconstructed by gridding. The coil sensitivity maps are then calculated using Walsh's method. (See Walsh et al. *Adaptive reconstruction of phased array MR imagery*. Magn Reson Med 2000; 43:682-690; and Griswold et al. *The use of an adaptive reconstruction or array coil sensitivity mapping and intensity normalization*. In Proceedings of the 10$^{th}$ Annual Meeting of ISMRM, Honolulu, Hi., USA, 2002., Abstract 2410, both of which are hereby incorporated by reference herein in their entirety as though fully set forth), which uses the eigenvector of the local signal covariance matrices as the estimate of the respective sensitivity values at the specific spatial location. The local image covariance matrices are averaged over 20×20×20 mm$^3$ blocks to suppress the streaking artifacts (one of skill in the art would readily appreciate that differently sized blocks could also be used). The averaging operation is implemented in MATLAB (The MathWorks, Natick, Mass.) using the graphical processing unit (GPU), which provided more than 50-fold acceleration compared with regular central processing unit (CPU) implementations. The noise covariance matrix in the SENSE framework is assumed to be an identity matrix. The sensitivity encoding operation is carried out using the gridding/regridding approach with a density compensation function (DCF) iteratively calculated from the k-space trajectory to compensate for sampling nonuniformity (See Pipe et al. *Sampling density compensation in MRI: rationale and an iterative numerical solution*. Magn Reson Med 1999; 41:179-186, which is incorporated herein by reference in its entirety as though fully set forth). Preconditioning by density compensation (See Pruessmann et al. *Advances in sensitivity encoding with arbitrary k-space trajectories*, Magn Reson Med 2001; 46:638-651, which is incorporated herein by reference in its entirety as though fully set forth) is used to significantly accelerate convergence of the CG iterations.

Stopping Criterion of the CG Iterations

Figure 10:
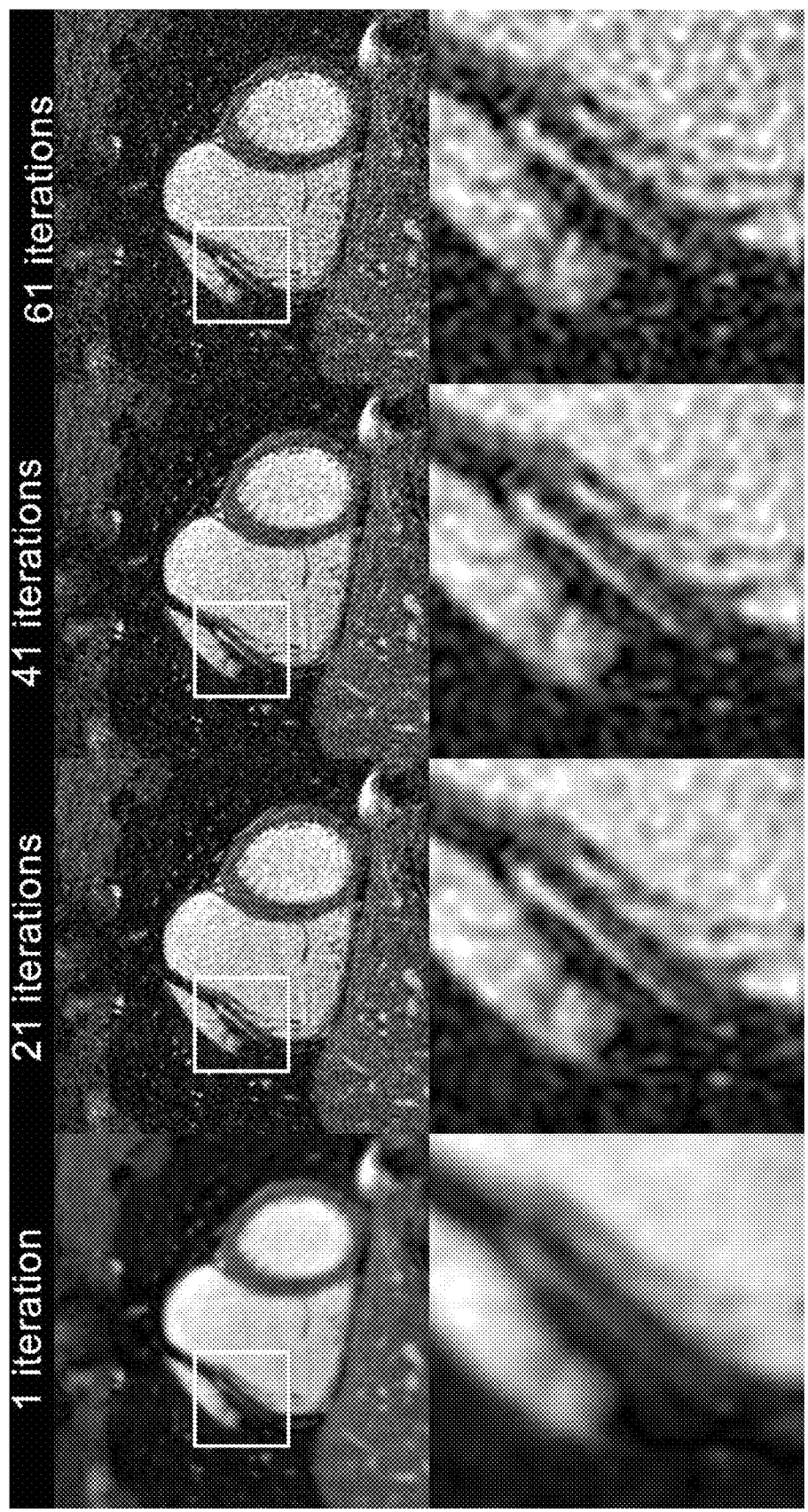
FIG. 10 demonstrates, in accordance with an embodiment of the invention, an example reconstruction with 10,000 projections showing the effect of iteration number on image sharpness and reconstruction noise. The first several iterations significantly improve the resolution while keeping noise level relatively low. However, after a certain point the additional noise amplification overwhelms any perceptible resolution improvement. For this example, the CG algorithm is stopped at 21 iterations.

The SENSE encoding matrix is generally ill-conditioned. However, the CO method is intrinsically regularized with the iteration number effectively acting as a regularization parameter. As a result, the CG-SENSE reconstruction demonstrates a weak convergence behavior: the iterations initially converge toward a solution with a certain image quality, but with subsequent iterations the aSNR deteriorates due to noise amplification. While not wishing to be bound by any one particular theory, in experiments, the inventors empirically found that a normalized residual of $\delta=0.01$ yields the overall best trade-off between regularization and noise amplification. In the reconstructed datasets, this residual level corresponded to 20-25 CG iterations, depending on the degree of k-space undersampling. FIG. 10 shows the effect of iteration number on image sharpness and aSNR.

Retrospective Undersampling.

Figure 11:
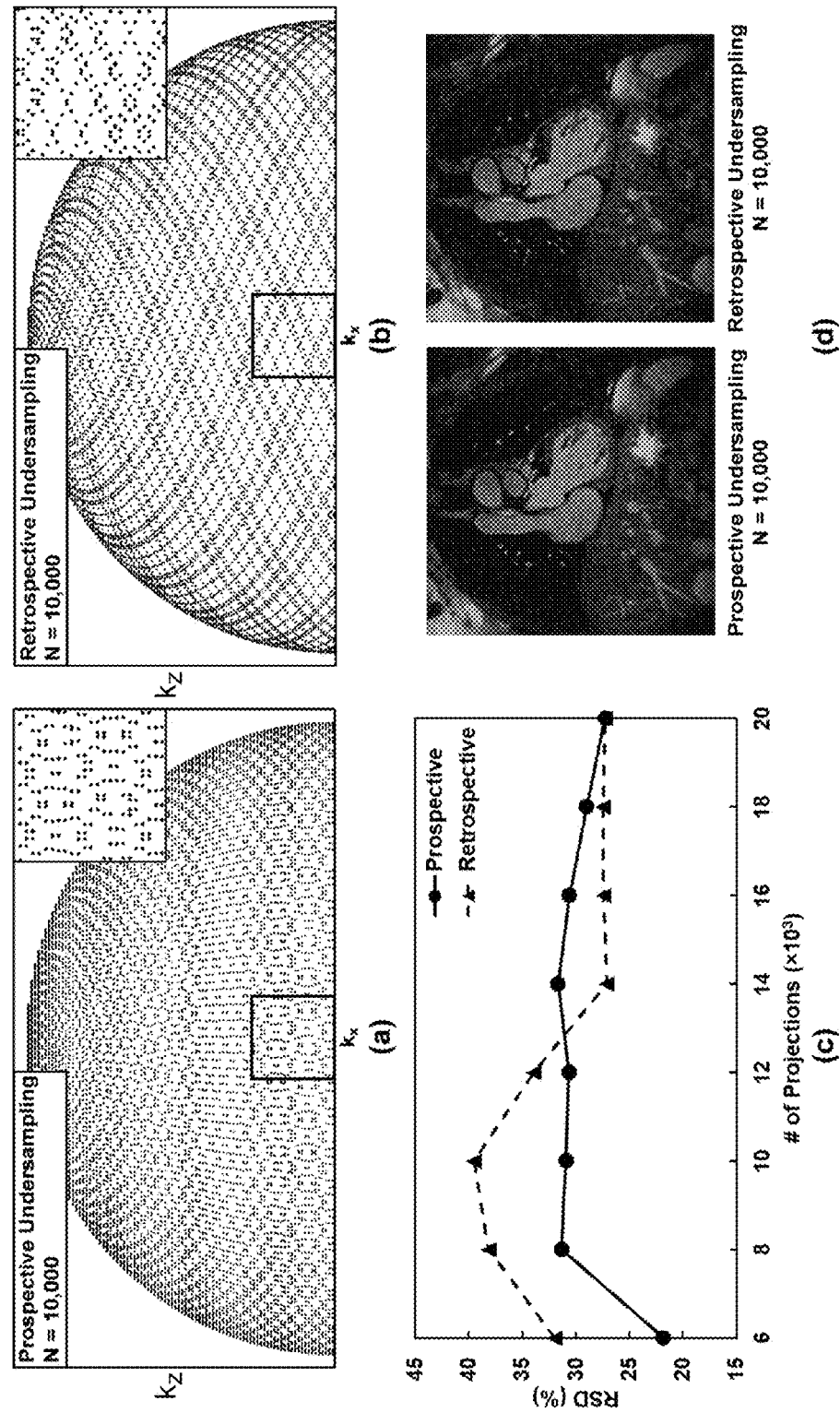
FIG. 11 demonstrates, in accordance with an embodiment of the invention, comparing prospective (a) and retrospective (b) undersampling with N=10,000 projections. Each dot represents the kx-kz coordinate of the starting point of a projection. The two display slightly different sampling patterns, as can be seen in the zoom-in view. c: For different numbers of projections, retrospective (dashed line) and prospective (solid line) undersampling show different RSD values, a measure of sampling uniformity. d: Based on experience, the sampling pattern difference has minimal effect on the final image quality, and should not alter the conclusion of this work.

Retrospective undersampling was performed to avoid the potential inter-scan variability associated with prospectively acquiring multiple undersampled datasets. The k-space trajectory is a slightly modified version of the "spiral on the sphere" (See Wong et al. *A strategy for sampling on a sphere applied to 3D selective RE pulse design*. Magn Reson Med 1994; 32:778-784, which is hereby incorporated herein by reference in its entirety as though fully set forth) trajectory used in several previous works (Stehning et al. *Fast isotropic volumetric coronary AIR angiography using free-breathing 3D radial balanced FFE acquisition*. Magn Reson Med 2004; 52:197-203; Stehning et al. *Free-breathing whole-heart coronary MRA with 3D radial SSFP and self-navigated image reconstruction*. Magn Reson Med 2005; 54:476-480; Bhat et al. *3D radial sampling and 3D affine transform-based respiratory motion correction technique for free-breathing whole-heart coronary MRA with 100% imaging efficiency*. Magn Reson Med. 2011; 65:1269-1277; and Pang et al. *Whole-heart coronary MRA with 100% respiratory gating efficiency: self-navigated three-dimensional retrospective image-based motion correction (TRIM)*. Magn Reson Med 2014; 71:67-74, all of which are hereby incorporated herein by reference as though fully set forth). Specifically, the k-space is divided into M interleaves, each one acquired over a certain number of heartbeats and containing N projections, whose origins form a spiral path on a sphere from one pole to the equator. The respective gradients are given by:

$$Gz(n) = \frac{(N-n)+0.5}{N} \quad \text{[EQUATION 5]}$$

$$Gx(n) = \frac{\cos\left(\frac{\sqrt{2N\pi}}{M}\sin^{-1}(Gz(n)) + m\theta_{GA}\right)}{\sqrt{1-Gz(n)^2}}$$

$$Gy(n) = \frac{\sin\left(\frac{\sqrt{2N\pi}}{M}\sin^{-1}(Gz(n)) + m\theta_{GA}\right)}{\sqrt{1-Gz(n)^2}}$$

where m=1, 2, 3 . . . M, n=1, 2, 3 . . . N, and $\theta_{GA}$ is the 111.25° golden-angle, by which each of the M interleaves is rotated azimuthally with respect to the preceding one. The azimuthal coverage of each interleaf was set to be 180' to traverse k-space frequently, therefore ensuring each respiratory bin to have uniform k-space coverage, at the same time minimizing the gradient jump to reduce eddy-current artifacts. With the golden-angle azimuthal increments between interleaves, the retrospective undersampling is achieved by simply throwing away all heartbeats after the first $N_i$ projections. As shown in the 10,000 projection example in FIG. 11, prospective and retrospective undersampling display slightly different sampling patterns. To measure the sampling uniformity, the relative standard deviation (RSD) of the distances between the projections' origins and their four nearest neighbors were calculated (See Piccini et al. *Spiral phyllotaxis: the natural way to construct a 3D radial trajectory in MRI*. Magn Reson Med 2011; 66:1049-1056, which is hereby incorporated herein by reference in its entirety as though fully set forth). As shown in FIG. 11C, depending on the number of projections, retrospective undersampling can have either higher or lower RSD than their prospective counterparts. Based on experience, the resulting changes in the respective point-spread-functions (SF) and hence aliasing patterns have minimal effect on the final image quality, as shown by the example in FIG. 11D.

Undersampling Factor Considerations

The 3DPR trajectory typically contains significantly fewer projections than what is required for alias-free imaging set by the Nyquist criterion. Effectively, a uniform angular undersampling reduces the size of the alias-free field of view (FOV) in the image domain according to the following square root relationship with respect to the number of acquired projections:

$$FOV_{alias-free} \propto \sqrt{N_{proj}} \quad \text{[EQUATION 6]}$$

To accommodate the wide spatial coverage from the nonselective excitation, a matrix size of $384^3$ and an isotropic FOV of 400 mm were used to minimize aliasing along the readout direction from peripheral signal sources such as the arms, the neck and the abdomen. Based on this matrix size, the number of projections to fulfill the Nyquist criterion is approximately 232,000, which is far from achievable in practice. However, assuming adequate magnetization-preparation across the excitation volume, the fat and muscle tissue will appear much darker than the brightest pixels from the ventricular blood pool. Therefore, streaks originating from the peripheral signal sources have lower intensity and consequently have minimal impact on the image quality within the central region-of interest (ROI). Because the heart spans less than one-third of the full FOV in all three dimensions, a relatively alias-free ROI can still be obtained if the alias-free FOV (Eq. [6]) is larger than the size of the heart. Based on this observation, 20,000 projections were used in the in vivo experiments as the maximally sampled reference, corresponding to an alias free FOV size of 120 mm and approximately 10 min of scan time. As an initial test, retrospective undersampling was performed on one maximally sampled dataset in 2000 projection decrements. Each dataset were then reconstructed using the CG-SENSE method, which were visually evaluated by an experienced reader to determine the required number of projections to achieve various image qualities relative to the reference ($N_0$): comparable to reference ($N_1$), lower but acceptable ($N_2$), and nondiagnostic ($N_3$). Gridding reconstruction was also performed for comparison.

Another potential source of image quality degradation is the accuracy of respiratory motion estimation. As suggested by previous works, around 40 heartbeats or 1000 projections are required in each respiratory bin for accurate image based motion estimation. While not wishing to be bound by any one particular theory, considering the distribution of data among the current six-bin setup is usually nonuniform, going below 10,000 projections will potentially lead to residual motion blurring due to inadequate motion correction for one or more respiratory bins.

In Vivo Experiments

Whole-heart coronary MRA data were collected on a clinical 1.5T scanner (MAGNETOM Avanto, Siemens AG Healthcare, Erlangen, Germany) using an ECG gated, T2-prepared and fat-saturated bSSFP pulse sequence with 3DPR trajectory and a 12-channel receiver coil array with the following parameters: TR/TE=3.2/1.6 ms, FOV=400 mm$^3$, matrix size=384$^3$, 200 µs nonselective hard pulse, flip angle=90°, readout bandwidth=900 Hz/pixel. Simple gradient delay correction was performed prospectively. A four-chamber CINE image was acquired after the initial localizers to determine the start and duration of the cardiac quiescent period. The cardiac trigger delay and the segment length were adjusted accordingly. No prospective respiratory gating was performed. A total number of 9 healthy volunteers (5 women, average age 29.2±9.1 years) were scanned with IRB approval and written consent. As discussed above, the maximally sampled dataset with $N_0$=20,000 projections was acquired for each subject. Retrospective undersampling was performed resulting in projection numbers $N_1$, $N_2$, and $N_3$. The resultant four datasets were then reconstructed offline using both the inventive method described above and motion-corrected gridding.

Offline reconstruction was implemented in MATLAB with around eight-fold computational acceleration using parallel computing toolbox on a workstation with a 12-core Intel Xeon CPU, 96 GB of memory, and an Nvidia Tesla C2050 GPU. The coronary images were reformatted using the CoronaViz software (Siemens Corporate Research, Princeton, N.J.). Subjective quality scores for all three major coronary artery branches, i.e., left anterior descending (LAD); left circumflex (LCX), and right coronary artery (RCA), were evaluated by two experienced readers blinded to the protocols on a four-point scale: 1: Poor, 2: Fair, 3: Good, 4: Excellent. The scores from the two readers were averaged before statistical analysis. Similar to several previous works on non-Cartesian coronary imaging, the inventors used apparent signal-to-noise-ratio (aSNR) as a quantitative measure of the overall image quality. The aSNR is calculated as the ratio between the blood signal intensity, measured within a circular ROI in the aorta at the level of the left coronary ostium, and the apparent noise level which is a blend of "true" noise and noise-like streaking and estimated from the signal standard deviation (SD) in an ROI placed on background air. A nonparametric statistical test (Wilcoxon's signed rank) was used for analyzing the subjective scores, and Student's t-test was used for analyzing aSNR measurements. 0.05 was used as the P-value threshold of statistical significance.

Results

As the 3DPR dataset became increasingly undersampled, gridding showed a higher level of streaking artifacts that rapidly deteriorated the aSNR. In contrast, the method largely maintained the image quality down to around 8000 projections, although more aggressive undersampling resulted in noticeable image blurring.

Figure 12:
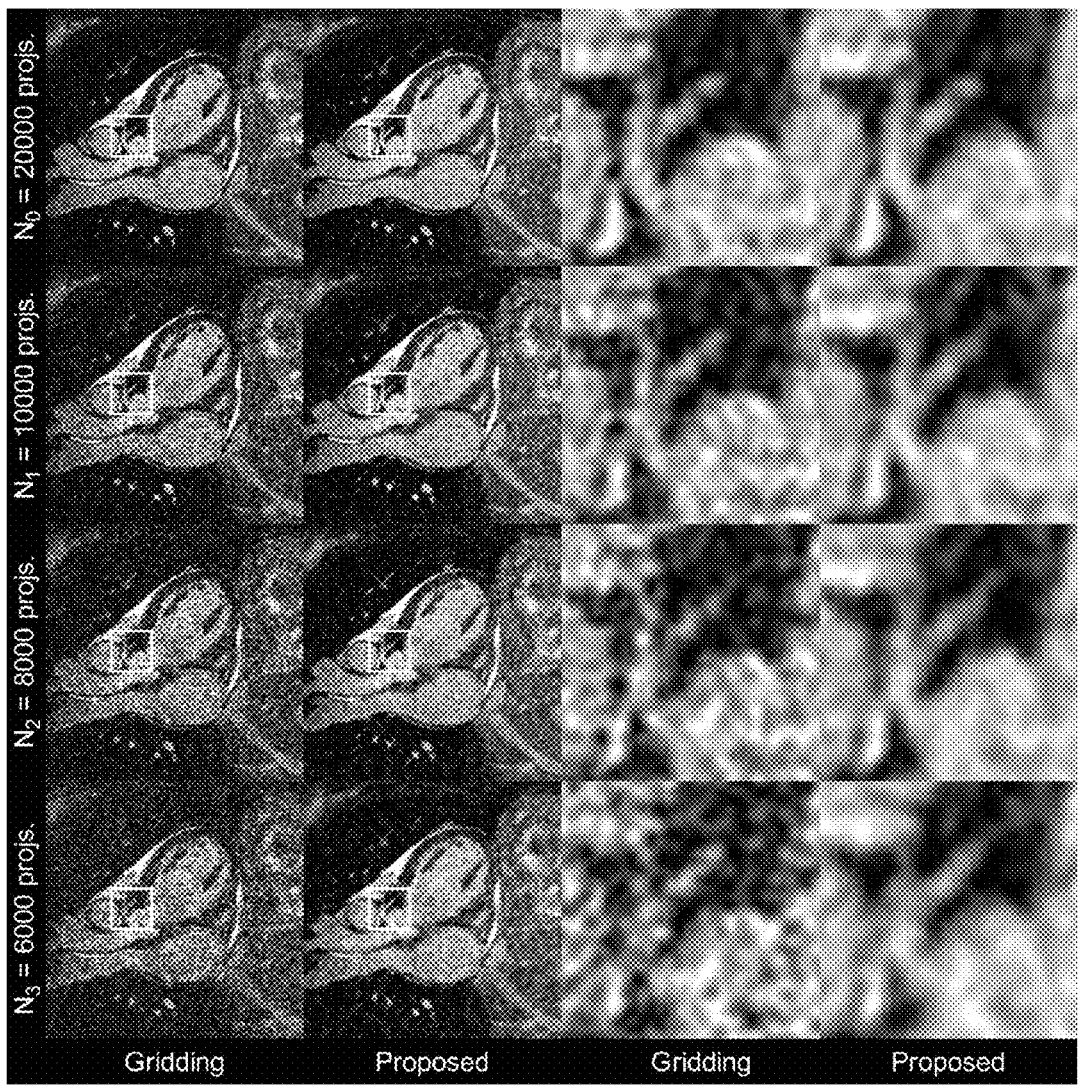
FIG. 12 demonstrates, in accordance with an embodiment of the invention, example images reconstructed using gridding (first row) and a novel method (second row) from 6000, 8000, 10,000 and 20,000 projections, with magnified coronal views of the left main coronary artery. As the projection number was reduced, the image quality with gridding quickly degraded, whereas with the novel method the image quality was largely maintained.

With the inventive method, as few as 10,000 projections provided visually identical image quality compared with the reference image with 20,000 projections; with 8,000 projections, reduced but still acceptable image quality was observed; yet further undersampling degraded the image quality to nondiagnostic. Therefore $N_1$ was set to be 10,000 projections, $N_2$ to be 8,000 projections, and $N_3$ to be 6,000 projections. The example shown in FIG. 12 demonstrates these observations in an example dataset.

Figure 13:
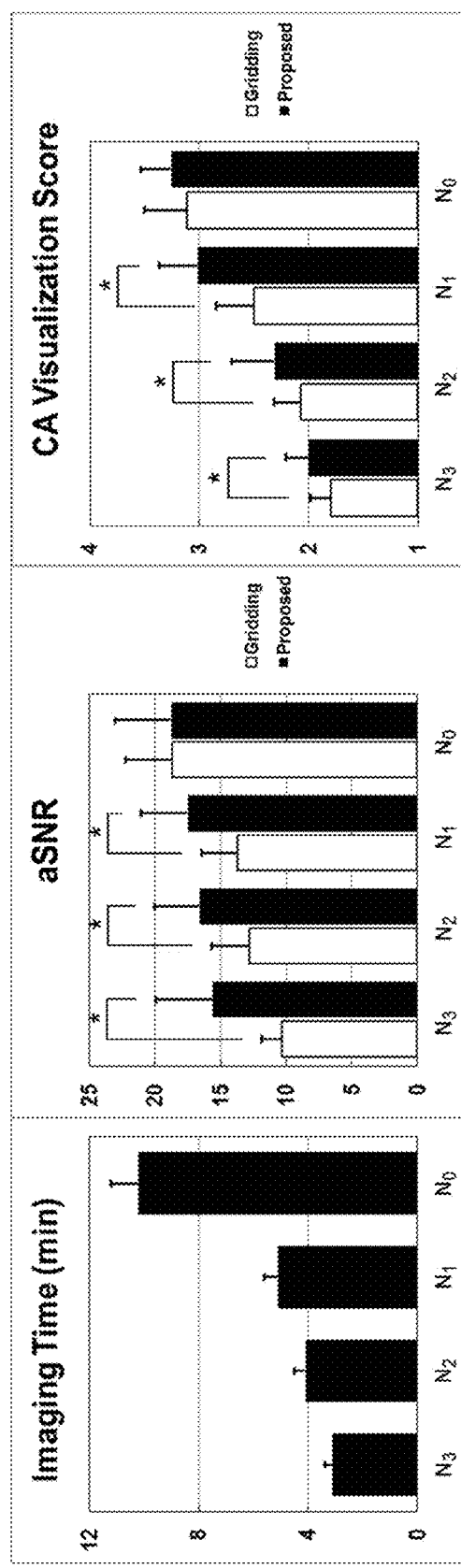
FIG. 13 demonstrates, in accordance with an embodiment of the invention, Left: Average imaging time for different projection numbers. $N_1$ (10,000 projections), $N_2$ (8,000 projections), and $N_3$ (6,000 projections) corresponded to scan time reductions by 50%, 61%, and 71% compared with $N_0$ (20,000 projections), respectively. Middle: Average aSNR values of gridding and the inventive method with different projection numbers. With the exception of $N_0$, the inventive method significantly improved the aSNR over gridding for a given number of projections. Notably, with the novel method, there was no significant difference between $N_1$ and $N_0$ despite the 50% reduction in scan time. Right: Average CA visualization scores of gridding and the inventive method with different projections numbers. Similarly, the inventive method significantly improved the score compared with gridding with the same number of projections. With the inventive method, $N_0$ showed a slight albeit significant advantage over $N_1$ (3.26 versus 3.02, P=0.008). Both scores are considered good. An asterisk (*) indicates statistical significance (P<0.05).
Figure 14:
FIG. 14 demonstrates, in accordance with an embodiment of the invention, reformatted images of three example subjects reconstructed by gridding and an inventive method with different projection numbers. Visually, the trend in image quality is in accordance with the numerical results. Comparing the two columns of each subject, the inventive method showed superior image quality to gridding. With 10,000 projections, the method offered nearly identical image quality to the maximally sampled image with 20,000 projections.

The imaging time of $N_0$ and the effective imaging times for $N_1$-$N_3$, defined as the sum of the duration of the heartbeats that would have been required by the shortened acquisition, were as follows: 10.2±1.0 min ($N_0$), 5.1±0.5 min ($N_1$), 4.1±0.4 min ($N_2$), and 3.1±0.3 min $N_3$). The average aSNR values were 18.7±3.6 (gridding, $N_0$) and 18.8±4.3 (inventive, $N_0$), 13.7±2.7 (gridding, $N_1$) and 17.5±3.5 (inventive, $N_1$), 12.8±2.8 (gridding, $N_2$) and 16.6±3.4 (inventive, $N_2$), and 10.3±1.5 (gridding, $N_3$) and 15.5±4.4 (inventive, $N_3$). For each projection number, the images reconstructed by the innovative method showed significantly higher aSNR than those by gridding. Notably, with the advanced reconstruction, the average aSNR of $N_1$ showed no significant difference compared with $N_0$, despite the two-fold undersampling. $N_2$ and $N_3$, however, showed significantly lower aSNR compared with $N_0$. The average coronary artery (CA) visualization scores were 3.11±0.39 (gridding, $N_0$) and 3.26±0.38 (inventive, $N_0$), 2.50±0.34 (gridding, $N_1$) and 3.02±0.41 (inventive, $N_1$), 2.07±0.24 (gridding, $N_2$) and 2.31±0.39 (inventive, $N_2$), and 1.80±0.19 (gridding, $N_3$) and 2.00±0.21 (inventive, $N_3$). Again, for each projection number, the inventive reconstruction yielded significantly higher average CA visualization scores than gridding. When comparing $N_1$ and $N_0$ using the inventive method, the maximally sampled $N_0$ demonstrated a slight albeit significant advantage over $N_1$. The average score for $N_0$ and $N_1$ were 3.26 and 3.02, respectively. With both scores in the "good" category, this result shows that the image quality was maintained undersampling from 20,000 to 10,000 projections, despite the 50% reduction in scan time. The results are summarized in FIG. 13. FIG. 14 shows the reformatted images from three example subjects with different reconstruction methods and numbers of projections. The observed image quality confirms the numerical results. The innovative method yielded superior aSNR and CA visualization compared with gridding, and reducing the number of projections from 20,000 to 10,000 only resulted in minimal degradation in image quality.

Discussion

As indicated above, the inventors developed a high-resolution free-breathing 3DPR scheme that uses self-calibrating CG-SENSE acceleration and retrospective affine motion correction. The performance of the developed method in whole-heart coronary MRA in terms of aSNR and subjective CA visualization scores at 1.0 mm$^3$ spatial resolution and different retrospective undersampling levels were evaluated. Results of the analysis were used to infer the optimal balance between the undersampling level and image quality. It was demonstrated that the innovative method significantly improves the aSNR and CA visualization scores compared with gridding. The achievable scan time was as low as 5 min while maintaining good image quality. In principle, a short acquisition time may also improve the robustness of whole-heart coronary MRA by reducing the chance of respiratory pattern drift, heart rate variation, and involuntary subject movement such as coughing and bulk motion during the scan.

Rather than prospectively acquiring the undersampled datasets separately, retrospective undersampling was performed on each 20,000-projection dataset to minimize the potential inter-scan variability that may confound the results. Based on experience, the sampling uniformity difference of prospective and retrospective undersampling was not critical in the scope of this work. However, in the presence of the often-conflicting requirements on sampling uniformity, eddy-current minimization, and frequent k-space traverse, trajectory optimization remains as an important topic and warrants continuing efforts.

Notably, no significant drop in aSNR was observed at $N_1=10,000$ projections compared with $N_0=20,000$ projections. Qualitatively speaking, this result indicates that at this particular undersampling level, the streaking suppression from the inventive parallel imaging reconstruction makes up for the accompanying noise amplification. However, using aSNR as a surrogate for true SNR has its limitations, the major one being that true noise and the noise-like streaking are not separated. Furthermore, as the noise amplification varies spatially due to parallel imaging, the true noise level in the signal ROI may be different than that of the background ROI. To reduce this potential error, the background ROI was positioned as close to the signal ROI as possible, and identical coil configurations for all subjects were used.

Several previous investigations have used 3DPR for whole-heart coronary MRA with potential advantages of volumetric coverage and isotropic resolution, respiratory self-navigation, and retrospective motion correction. With gridding reconstruction, the streaking artifacts from angular undersampling adversely affect the image quality. To alleviate this problem, advanced reconstruction strategies have been explored previously, including self-calibrated k-space parallel imaging (GRAPPA) and coil-by-coil compressed sensing (CS) reconstruction with GPU implementation. The innovative method described in this section uses a flexible k-space motion correction scheme that can be integrated into the CG-SENSE framework in a straightforward manner. However, other advanced reconstruction methods may also apply. Merely by way of example, the innovative method does not currently impose any explicit L1 regularization, commonly used in CS type reconstructions to exploit image sparsity in certain transform domains. A recent work by Akcakaya et al compared Cartesian CS and parallel imaging, and concluded that the former is more suitable for low SNR applications such as high resolution coronary MRA, Future investigations are warranted to compare the performance of the inventive non-Cartesian parallel imaging method, CS, and potentially a combination of the two. It is also worth exploring the benefit of more sophisticated motion models, such as nonrigid deformation, that may further improve the accuracy of respiratory motion modeling while still can be incorporated into the encoding operations. In some embodiments, the methods described herein will benefit from coil arrays with more receiver elements, such as a 32-channel coil, which offer higher baseline SNR and alleviated coil geometry constraints. Additionally, the increased flexibility in selecting different coil elements will help reducing the overall sensitivity to any bright peripheral signal sources, such as insufficiently suppressed fat tissue due to $B_0$ or $B_1$ inhomogeneity, and thus lowering the streaking level in the central heart ROI. The major practical issue with using more coil elements is the elevated computational burden. For the 12-channel setup described herein, the complex double coil sensitivity matrix has a size of around 10 GB, and the CG-SENSE reconstruction requires around 80 GB of free memory space. The current reconstruction time is around 1.5-2 h including motion correction, sensitivity map estimation, and the CG-SENSE iterations. To address the memory demand associated with even larger receiver coil arrays, at least two solutions can be explored in the future. First, channel compression can be performed to reduce the computational demand without significant negative effect on image quality. Second, by excluding some of the coil elements that are mainly sensitive to peripheral FOV, one can potentially reduce the readout oversampling factor without introducing significant aliasing. Indeed, decreasing the number of readout points from 384 to 256 will shrink the raw image matrix by over 70%, thus greatly alleviating the memory requirement.

Finally, in some embodiments, the method described herein offers a flexible framework that can be applied to many scenarios that require accelerated acquisition with wide coverage and isotropic resolution. For example, following the successful demonstration in this work on non-contrast coronary MRA, the developed framework can be readily generalized to contrast-enhanced coronary MRA with inversion recovery prepared spoiled gradient echo, the current method of choice for 3T. A major challenge with the conventional protocol is that the unpredictable scan time and variable contrast dynamics makes it difficult to synchronize the k-space center acquisition with maximum coronary artery enhancement. With 3DPR, careful prospective timing becomes unnecessary as the contrast dynamics can be retrospectively monitored either from the self-navigation profiles or a series of 3D time-resolved images. The data collected during rapid contrast change or the wash out phase can be simply discarded. Meanwhile, effort should be made to optimize the contrast injection strategy to maintain a stable blood pool enhancement during the scan time to minimize significant intensity modulation to the 3DPR k-space or disruption of the self-navigation profiles.

Conclusions

A 3DPR based coronary MRA protocol was developed that combines self-calibrating CG-SENSE reconstruction and self-navigated respiratory motion correction with 100% acquisition efficiency. Results presented herein demonstrate that the method described herein significantly improves the image quality compared with motion corrected gridding reconstruction. Moreover, the in vivo studies indicate that good image quality can be achieved with 5 min of scan time in healthy volunteers.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for performing magnetic resonance imaging (MRI) on a subject, comprising performing one or more of the following scans using an MRI machine:
    (a) a scout scan to determine the position of the subject's heart;
    (b) a stress perfusion MRI scan on the subject's heart;
    (c) a cine MRI scan on the subject's heart;
    (d) a rest perfusion MRI scan on the subject's heart;
    (e) a coronary MRA scan on the subject's heart; and
    (f) a delayed enhancement MRI scan on the subject's heart; wherein (a) one or more scan is performed by using a continuous three dimensional radial acquisition scheme that results in the acquisition of a free-breathing k-space dataset, and (b) image reconstruction for one or more scan is performed using a constrained or compressed sensing scheme, and wherein the method does not require (1) ECG triggering, (2) breath-holding by the subject, or (3) the use of a diaphragm navigator.

2. The method of claim 1, further comprising performing T2-weighted imaging for edema imaging of the subject's heart and/or performing T1-weighted imaging for fibrosis imaging of the subject's heart.

3. The method of claim 1, wherein the image reconstruction for one or more scans comprises conjugate-gradient sensitivity encoding (CG-SENSE) reconstruction.

4. The method of claim 1, further comprising correcting for the subject's motion during one or more scans by a method comprising:
    (1) segmenting an acquired free-breathing k-space data set into different respiratory bins using self-navigation;
    (2) using a single bin as a reference, estimating the respiratory motion of all other bins using image-based 3D affine registration; and
    (3) using estimated translation vectors and affine transform matrices to modify the k-space data and trajectory, thereby resulting in motion-corrected k-space data and trajectory.

5. The method of claim 4, further comprising incorporating the resulting motion-corrected k-space data and trajectory into a CG-SENSE reconstruction framework.

6. The method of claim 5, further comprising performing sensitivity self-calibration by a method comprising:
    (1) reconstructing motion-corrected individual coil images by gridding;
    (2) calculating coil sensitivity maps by using the eigenvector of local signal covariance matrices as the estimate of the respective sensitivity values at a specific spatial location; and
    (3) averaging the local image covariance matrices over blocks of a predetermined size to suppress streaking artifacts.

7. The method of claim 6, wherein the averaging operation is implemented in MATLAB using a graphical processing unit (GPU).

8. The method of claim 7, wherein the sensitivity encoding operation is performed using a gridding/regridding approach with a density compensation function (DCF) iteratively calculated from the k-space trajectory to compensate for sampling nonuniformity.

9. The method of claim 8, further comprising preconditioning by density compensation to accelerate convergence of the CG iterations.

10. The method of claim 9, further comprising introducing a contrast agent into the subject's vascular system prior to or during any of one or more of scans a-f.

11. The method of claim 10, further comprising diagnosing the subject with the presence or absence of a cardiovascular disease or condition based upon one or more resulting images.

12. The method of claim 11, wherein the cardiovascular disease is atherosclerosis and/or cardiomyopathy.

13. The method of claim 11, wherein the MRI machine is a 1.5T scanner or a 3T scanner.

14. A magnetic resonance imaging system, comprising:
(1) a magnet operable to provide a magnetic field;
(2) a transmitter operable to transmit to a region within the magnetic field;
(3) a receiver operable to receive a magnetic resonance signal from the region; and
(4) a processor operable to control the transmitter and the receiver; wherein the processor is configured to direct the transmitter and receiver to execute a sequence, comprising (a) acquiring magnetic resonance data from a volume of interest (VOI) comprising all or a portion of the subject's heart according to the method of claim 1; and (b) generating one or more images using the image reconstruction scheme of claim 1, wherein a processor of the MRI machine and/or a subsystem configured to function therewith are configured to generate one or more images based on the magnetic resonance data acquired.

15. A non-transitory machine-readable medium having machine executable instructions for causing one or more processors of a magnetic resonance imaging (MRI) machine, and/or a subsystem configured to function therewith, to execute a method, comprising:
performing one or more of the following scans:
(a) a scout scan to determine the position of a subject's heart;
(g) a stress perfusion MRI scan on the subject's heart;
(h) a cine MRI scan on the subject's heart;
(i) a rest perfusion MRI scan on the subject's heart;
(j) a coronary MRA scan on the subject's heart; and
(k) a delayed enhancement MRI scan on the subject's heart; wherein (a) one or more scan is performed by using a continuous three dimensional radial acquisition scheme that results in the acquisition of a free-breathing k-space dataset, and (b) image reconstruction for one or more scan is performed using a constrained or compressed sensing scheme, and wherein the method does not require (1) ECG triggering, (2) breath-holding by the subject, or (3) the use of a diaphragm navigator.

16. The non-transitory machine-readable medium of claim 15, wherein the method executed further comprises performing T2-weighted imaging for edema imaging of the subject's heart and/or performing T1-weighted imaging for fibrosis imaging of the subject's heart.

17. The non-transitory machine-readable medium of claim 15, wherein the image reconstruction for one or more scans comprises conjugate-gradient sensitivity encoding (CG-SENSE) reconstruction.

18. The non-transitory machine-readable medium of claim 17, wherein the method executed further comprises correcting for the subject's motion during one or more scans by a method comprising:
(1) segmenting an acquired free-breathing k-space data set into different respiratory bins using self-navigation;
(2) using a single bin as a reference, estimating the respiratory motion of all other bins using image-based 3D affine registration; and
(3) using estimated translation vectors and affine transform matrices to modify the k-space data and trajectory, thereby resulting in motion-corrected k-space data and trajectory.

19. The non-transitory machine-readable medium of claim 18, wherein the executed method further comprises incorporating the resulting motion-corrected k-space data and trajectory into a CG-SENSE reconstruction framework.

20. The non-transitory machine-readable medium of claim 19, wherein the method executed further comprises performing sensitivity self-calibration by a method comprising:
(1) reconstructing motion-corrected individual coil images by gridding;
(2) calculating coil sensitivity maps by using the eigenvector of local signal covariance matrices as the estimate of the respective sensitivity values at a specific spatial location; and
(3) averaging the local image covariance matrices over blocks of a predetermined size to suppress streaking artifacts.

* * * * *